United States Patent
Link et al.

(10) Patent No.: US 11,732,013 B2
(45) Date of Patent: Aug. 22, 2023

(54) ASTEXIN PEPTIDES

(71) Applicant: The Trustees of Princeton University, Princeton, NJ (US)

(72) Inventors: A. James Link, Belle Meade, NJ (US); Mikhail O. Maksimov, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 168 days.

(21) Appl. No.: 17/128,632

(22) Filed: Dec. 21, 2020

(65) Prior Publication Data

US 2021/0107950 A1    Apr. 15, 2021

Related U.S. Application Data

(60) Division of application No. 16/057,292, filed on Aug. 7, 2018, which is a continuation of application No. 14/424,617, filed as application No. PCT/US2013/057203 on Aug. 29, 2013, now Pat. No. 10,072,048.

(60) Provisional application No. 61/695,772, filed on Aug. 31, 2012, provisional application No. 61/839,493, filed on Jun. 26, 2013.

(51) Int. Cl.
| | |
|---|---|
| C07K 14/195 | (2006.01) |
| A01N 63/50 | (2020.01) |
| A62D 3/33 | (2007.01) |
| C02F 1/28 | (2023.01) |
| A62D 101/43 | (2007.01) |
| C02F 101/20 | (2006.01) |

(52) U.S. Cl.
CPC ............ *C07K 14/195* (2013.01); *A01N 63/50* (2020.01); *A62D 3/33* (2013.01); *C02F 1/286* (2013.01); *A62D 2101/43* (2013.01); *C02F 2101/20* (2013.01)

(58) Field of Classification Search
None
See application file for complete search history.

(56) References Cited

U.S. PATENT DOCUMENTS 10,072,048 B2 *  9/2018  Link .................... C07K 14/195
10,927,152 B2 *  2/2021  Link ........................ A62D 3/33

OTHER PUBLICATIONS

Knappe et al., "Introducing Lasso Peptides as Molecular Scaffolds for Drug Design: Engineering of an Integrin Antagonist," Angew. Chem. Int. Ed., 2001, 50, 8714-8717.
Maksimov et al., "Lasso Peptides: Structure, Function, Biosynthesis, and Engineering," Nat. Prod. Rep., 2012, 29, 996-1006.
Maksimov et al., "Discovery and Characterization of an Isopeptidase That Linearizes Lasso Peptides," J. Am., Chem. Soc., 2013, 135, 12038-12047.
NBCI, GenBank Accession No. YP_004088035.1 (Apr. 12, 2012), 1-3.
NBCI, GenBank Accession No. PDB: 2LTI_A (Sep. 5, 2012).
NBCI, GenBank Accession No. PDB: 2M8F_A (Jul. 31, 2013).
Pan et al., "Sequence Diversity in the Lasso Peptide Framework: Discovery of Functional Microcin J25 Variants with Multiple Amino Acid Substitutions," J. Am. Chem. Soc., 2011, 133, 5016-5023.
Zimmermann M. et al. "The astexin-1 lasso peptides: biosynthesis, stability, and structural studies."; Chem. Biol. 20:558-569(2013).
Hegemann et al. Lasso Peptides: An Intriguing Class of Bacterial Natural Products. Acc. Chem. Res. 2015, 48, 1909-1919.
Link et al. Novel Lasso Peptides as Molecular Scaffolds for Protein Therapeutics, Molecular Sensors, and Probes. Web Published 2013. http://puotl.technologypublisher.com/technology/12649.
USPTO "Nature-Based Product" Examples (Dec. 16, 2014); Example 3 Amazonic Acid, Claim 1; https://www.uspto.gov/patents/law/exam/mdc_examples_Nature-based_products.pdf.
Maksimov M.O., Pelczer I. , Link A.J.; "Precursor-centric genome-mining approach for lasso peptide discovery" Proc. Natl. Acad. Sci. U.S.A. 109:15223-15228(Jun. 25, 2012).
Maksimov M.O., Pelczer I. , Link A.J.; "Precursor-centric genome-mining approach for lasso peptide discovery."; Proc. Natl. Acad. Sci. U.S.A 109:15223-15228(2012).

* cited by examiner

*Primary Examiner* — Maury A Audet
(74) *Attorney, Agent, or Firm* — Meagher Emanuel Laks Goldberg & Liao, LLP

(57) ABSTRACT

Provided are astexin-1, astexin-2 and astexin-3 lasso peptides, which are based on sequences identified in *Asticaccaulis excentricus*, and methods of making and using same. Astexin-1 is highly polar, in contrast to many lasso peptides that are primarily hydrophobic, and has modest antimicrobial activity against *Caulobacter crescentus*, a bacterium related to *Asticaccaulis excentricus*. The solution structure of astexin-1 was determined, revealing a unique topology that is stabilized by hydrogen bonding between segments of the peptide. Astexins-2 and -3 are intracellular lasso peptides.

18 Claims, 12 Drawing Sheets

Specification includes a Sequence Listing.

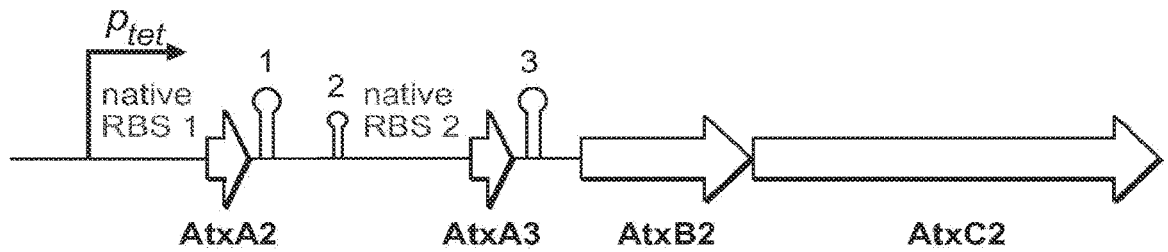
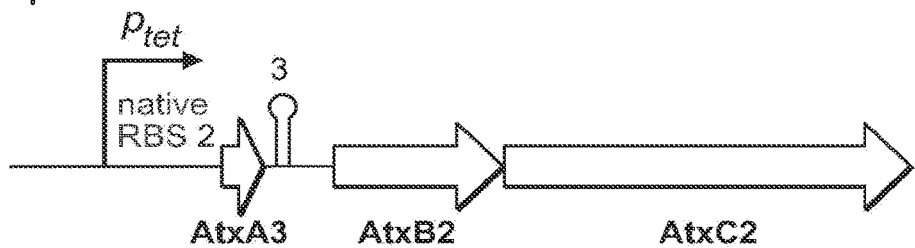
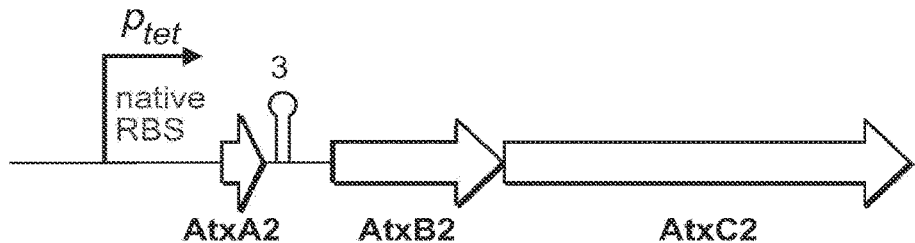
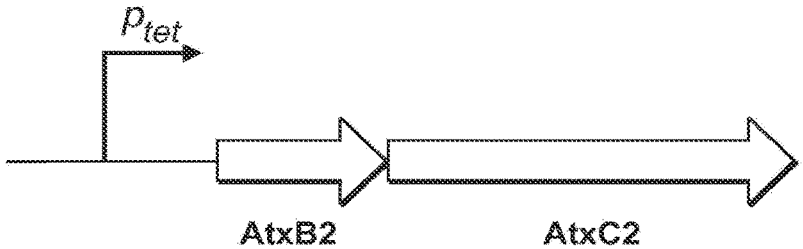
FIG. 2

FIG. 5C  AtxE2 versus astexin-3
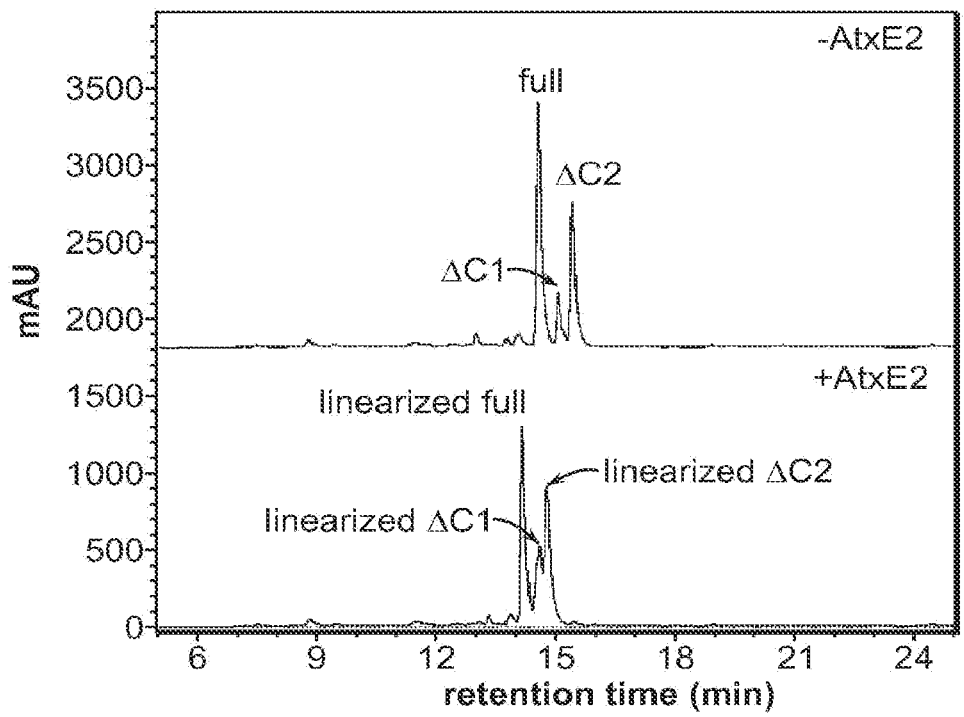
FIG. 5D  AtxE2 versus astexin-3
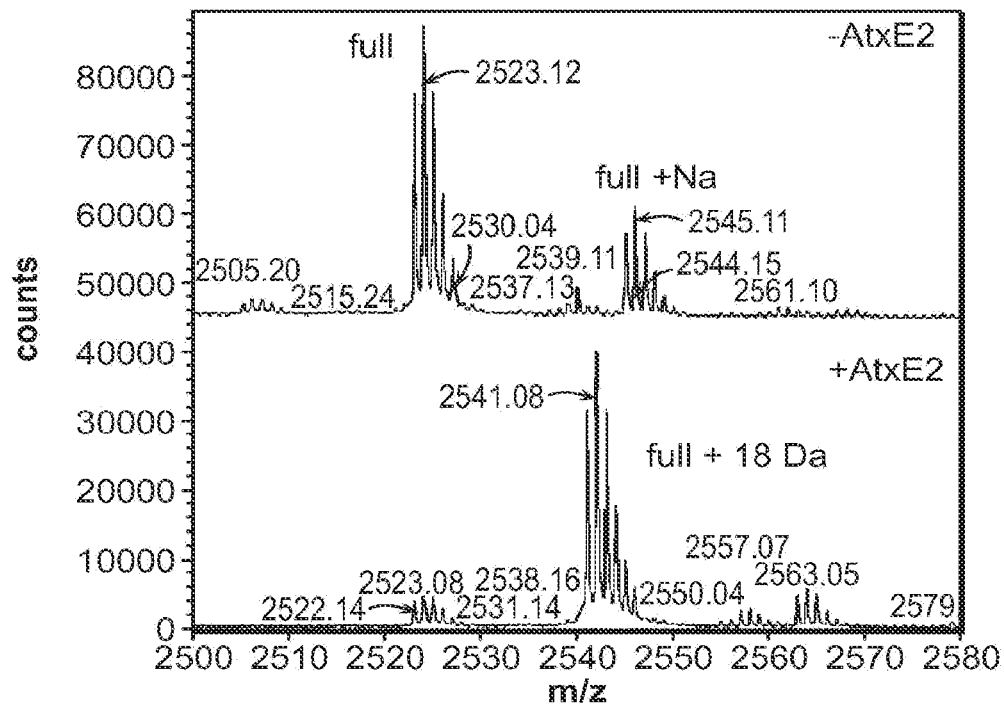

US 11,732,013 B2

ASTEXIN PEPTIDES

RELATED APPLICATIONS

This application claims priority to U.S. Ser. No. 61/695,772, filed Aug. 31, 2012, and U.S. Ser. No. 61/839,493, filed Jun. 26, 2013. The contents of these applications are incorporated by reference in their entireties.

STATEMENT AS TO FEDERALLY SPONSORED RESEARCH

This invention was made with government support under Grant CBET-0952875 awarded by the National Science Foundation. The government has certain rights in the invention.

BACKGROUND

Lasso peptides are a class of ribosomally-derived natural products with diverse bioactivities. The characteristic threaded lasso structure in these peptides derives from an isopeptide bond attaching the N-terminus of the peptide to an acidic sidechain.

SUMMARY

The invention provides a family of low molecular weight lasso peptides termed astexin-1, astexin-2, and astexin-3 (collectively, "astexin peptides"), which were are derived from a bacterial source. Molecules of this class are highly stable, engineerable, and, therefore, attractive as molecular scaffolds.

The invention provides astexin peptides and polynucleotides that encode astexin peptides—astexin-1, astexin-2 and astexin-3, as well as the peptides encode by these polynucleotides. The peptides are single lasso peptide predicted to be produced by the freshwater bacterium *Asticcaulis excentricus*. Molecules of this class are highly stable, engineerable and therefore attractive as molecular scaffolds.

Astexin-1 is among the largest lasso peptide isolated to date. It is also highly polar, in contrast to many lasso peptides that are primarily hydrophobic. Astexin-1 has modest antimicrobial activity against *Caulobacter crescentus*, a bacterium related to *Asticcaulis excentricus*. The solution structure of astexin-1 was determined, revealing a unique topology that is stabilized by hydrogen bonding between segments of the peptide.

Astexins-2 and -3 are intracellular lasso peptides that are not exported into the extracellular medium like astexin-1. Astexins-2 and -3 are identical in length and are the largest molecules in the lasso peptide family. Their natural amino acid sequences are highly polar, which stands in contrast to the hydrophobic composition of other members of its class. Astexin-3 has natural tryptophan fluorescence, which facilitates monitoring of this molecule during in vitro assays.

Unless indicated otherwise, reference to an astexin peptide is understood to refer to an astexin-1, astexin-2 and/or an astexin-3 peptide.

Also provided by the invention is a lasso isopeptide hydrolase, named AtxE2. AtxE2 has been found to selectively cleave astexin-2 and astexin-3 peptides. It is the first described lasso isopeptide hydrolase.

Astexin peptides and AtxE2 polypeptides can be produced using methods known in the art. In one embodiment, astexin peptides are made following the basic schema of heterologous protein expression. An engineered gene cluster, placed inside a gene delivery system (plasmid), is transformed into *E. coli* by chemical transformation or by electroporation. These plasmid-bearing cells are grown at appropriate experimental conditions and induced to express astexin-1 biosynthesis genes by the addition of a small molecule at a specific time in the life cycle of the *E. coli*. At the end of the expression period the *E. coli* cells are separated from their growth media by centrifugation. The cells are lysed, boiled and the lysates are extracted using a solid phase extraction system. Astexin peptides are then purified from this crude extract to a desired purity using preparatory HPLC.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention are apparent from the following description, and from the claims.

BRIEF DESCRIPTION OF THE DRAWINGS

FIG. 2: Engineered gene clusters for the production of astexins-2, -3. DNA inverted repeats are shown as stem-loop structures.

FIG. 5A-D: HPLC and MALDI-MS analysis of astexin-2 and astexin-3 extracts before and after treatment with isopeptidase AtxE2. A: The retention times of lassoed, threaded astexin-2 species increases after incubation with AtxE2. Unthreaded astexin-2 species retention times do not change. B: MS spectra confirm hydrolysis of astexin-2 ΔC3. C: The retention times of astexin-3 species decrease after AtxE2 treatment. D: The hydrolysis of astexin-3 was confirmed by MS.

DESCRIPTION

Figure 1:
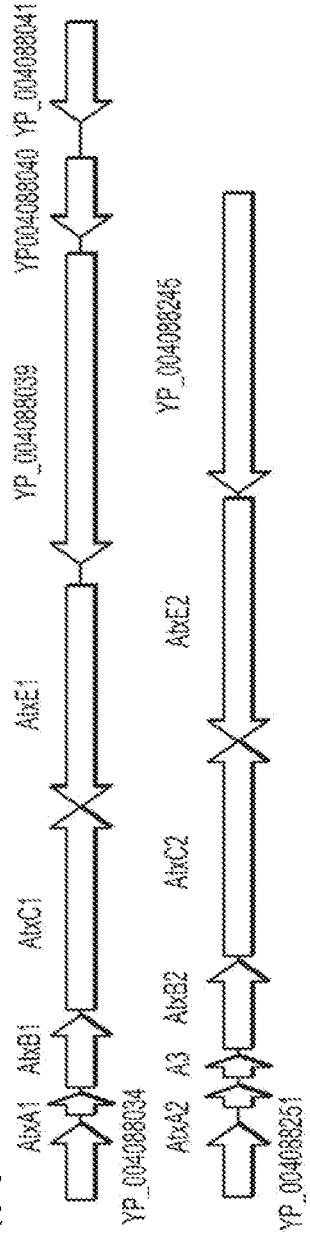
FIG. 1A-C: Lasso peptides in *Asticcacaulis excentricus*. A: The architecture of the astexin-1 and astexin-2, -3 lasso peptide gene clusters. Genes required for the biosynthesis are shown in blue, while other conserved genes are highlighted in red. B: Homology of lasso peptide cluster associated genes to known protein families. C: Precursor alignment of astexins-1, -2, and -3.
Figure 3A:
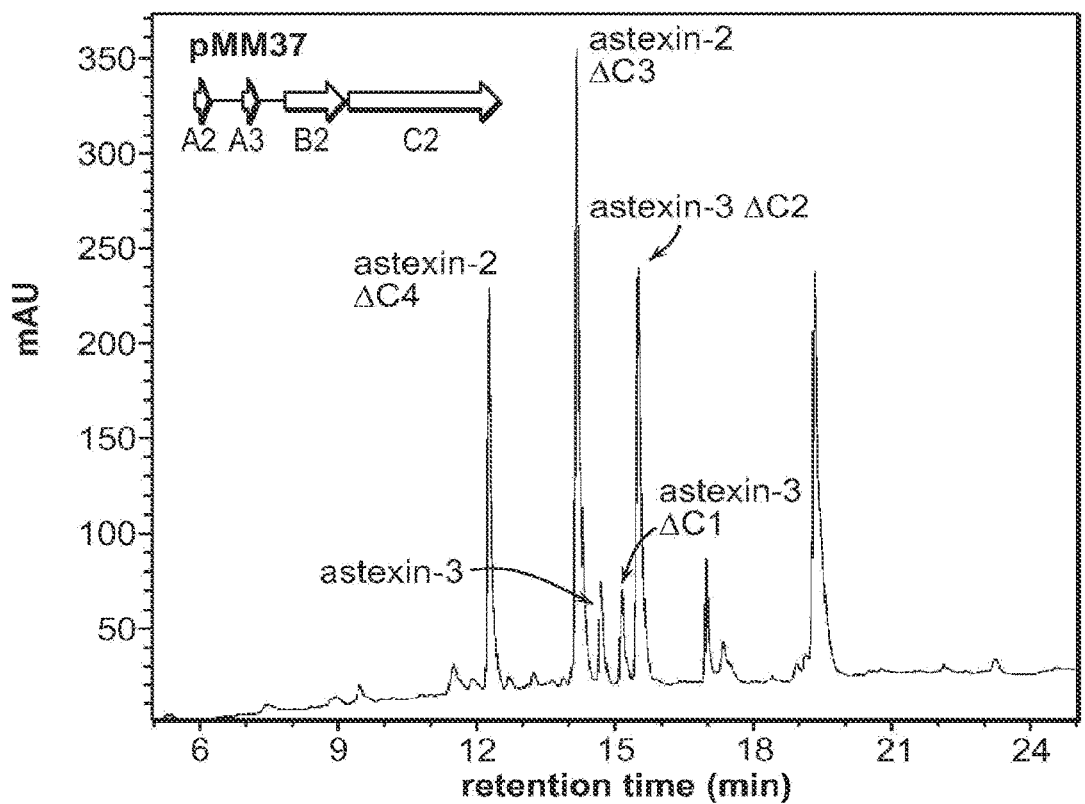
FIG. 3A-D: HPLC chromatograms of lysate extracts of pMM37, pMM38, pMM39 and pMM40 bearing cells. C-terminal truncation variants are indicated such that ΔC2 indicates that the 2 C-terminal amino acids have been removed. A: The pMM37 dual precursor construct produces variants of astexin-2 and astexin-3. B: No peptides of interest are expressed from the pMM38 control construct. C,D: The single precursor constructs, pMM39 and pMM40, produce variants of astexin-3 and astexin-2 respectively. Unthreaded ΔC3 and ΔC4 astexin-2 are observed in (A) and (D) and labeled. No species corresponding to unthreaded astexin-3 are observed.
Figure 3B:
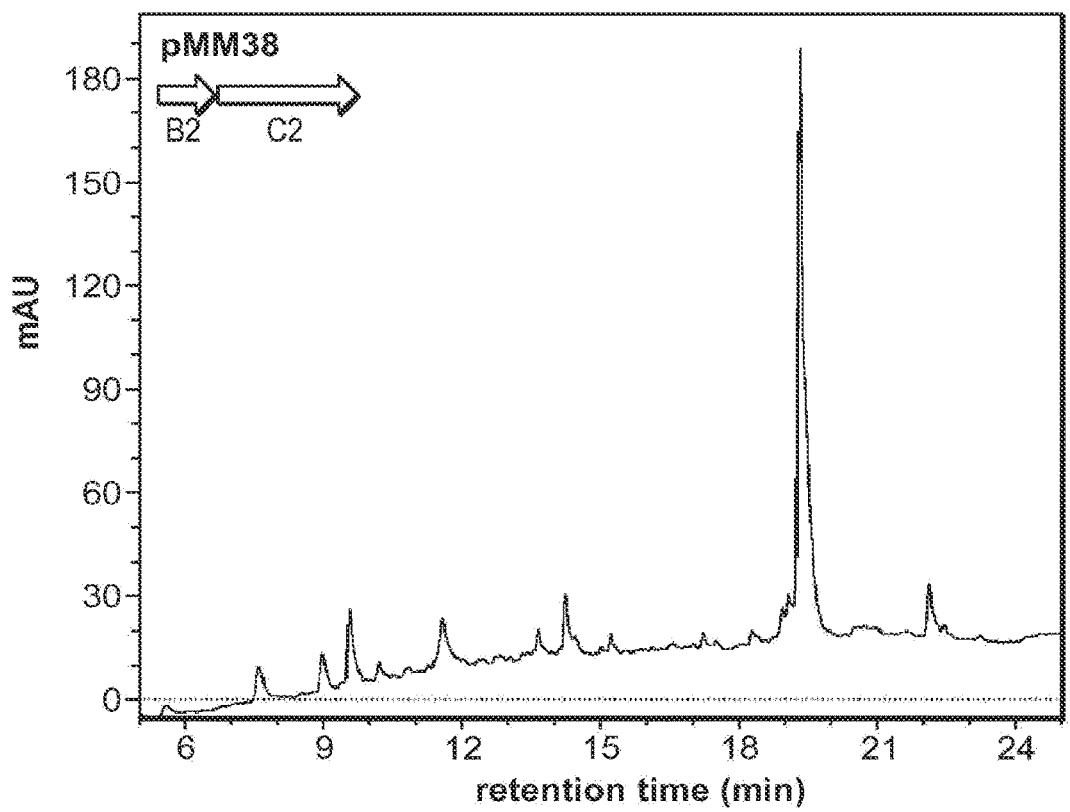
Figure 3C:
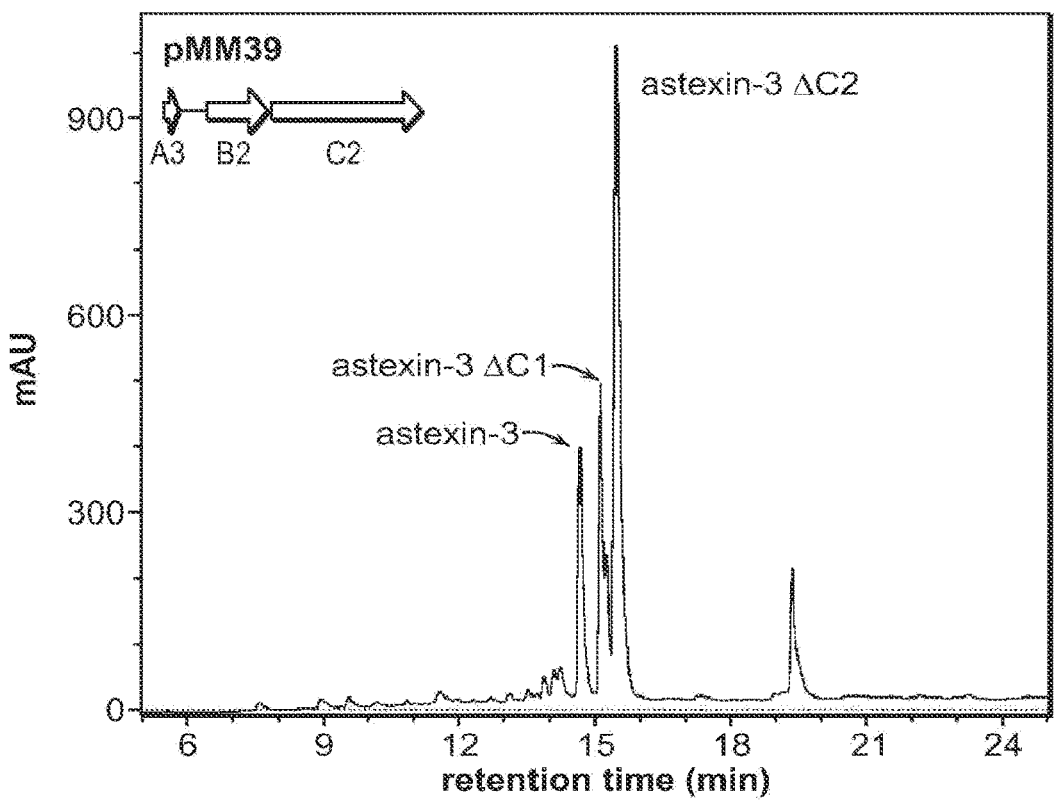
Figure 3D:
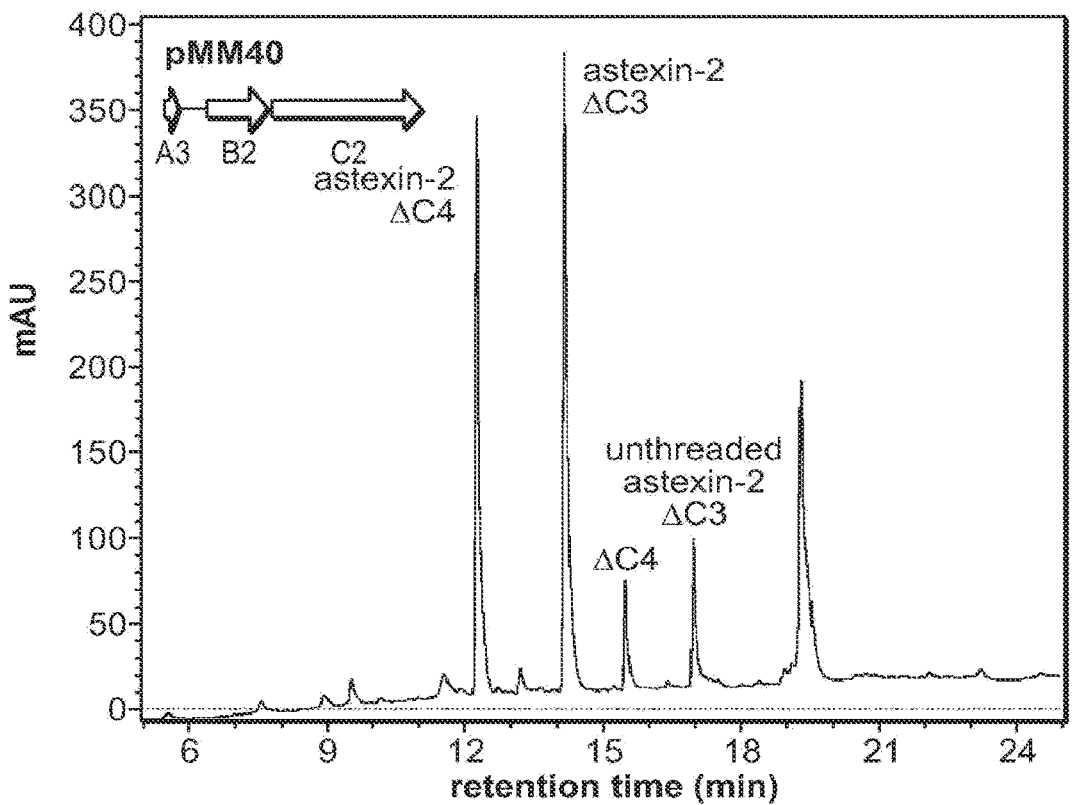

Ribosomally-synthesized and posttranslationally modified peptides (RiPPs) are a rapidly growing superfamily of natural products that originate from gene encoded polypeptides[1]. The rapid growth in the discovery of RiPPs has been facilitated by genome mining approaches that reveal RiPP gene clusters within sequenced organisms[2]. Lasso peptides are a class of RiPPs that consist of ca. 20 amino acid-long chains that are folded into a structure resembling a threaded lasso[3]. An isopeptide bond installed between the N-terminus of the peptide and a Glu or Asp sidechain holds the topologically constrained structure together. To date these genome mining studies have focused solely on four genes in lasso peptide gene clusters: the A gene encoding the lasso peptide precursor, the B and C genes encoding maturation enzymes, and the D gene which encodes an ABC transporter[8-10]. Our global lasso peptide genome mining data[4] hinted that there may be other genes associated with lasso peptide regulation or modification beyond these four canonical genes.

The astexin peptides of the invention are additionally useful as, e.g. receptor antagonists, enzyme inhibitors, and as inhibitors of viral fusion. The peptides of the invention can also be used in peptide therapeutics, as molecular sensors for disease diagnostics, and as molecular probes for biochemical research.

This line of inquiry led us to examine the immediate genomic neighborhood of two lasso peptide gene clusters found in the freshwater bacterium *Asticcacaulis excentricus*. Here we report the heterologous expression of astexin-2 and astexin-3, the two lasso peptides encoded on chromosome 2 of *A. excentricus*. The structure of astexin-3 was determined by NMR. Both of these clusters lack the ABC transporter found in the gene clusters of the lasso peptides microcin J25, capistruin, and lariatin[5,9,11]. Instead, these clusters include divergently transcribed genes (AtxE1 and AtxE2) annotated as proteases immediately downstream of the genes encoding the lasso peptide maturation enzymes. The protease AtxE2 specifically cleaves the isopeptide bond of lasso peptides encoded in the neighboring cluster. The cleavage reaction proceeds only on threaded lasso peptides.

An evolutionary bioinformatics analysis revealed that many known and putative lasso peptide gene clusters segregate into two distinct clades delineated by the presence of either an ABC transporter or a lasso peptide isopeptidase.

Astexin Peptides

The invention provides astexin-1, astexin-2, and astexin-3 peptides.

An astexin-1 peptide of the invention includes a substantially purified peptide based on the following amino acid sequence:

$H_2N-X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-X^{19}-X^{20}-X^{21}-X^{22}-X^{23}-X^{24}-COOH$, wherein $X^1$ is absent or a peptide sequence or a naturally or non-naturally occurring amino acid;

$X^2$ is absent or G or a small naturally or non-naturally occurring amino acid;

$X^3$ is absent or L or a hydrophobic or a small naturally or non-naturally occurring amino acid;

$X^4$ is absent or S or a polar naturally or non-naturally occurring amino acid;

$X^5$ is absent or Q or a polar or acidic naturally or non-naturally occurring amino acid;

$X^6$ is absent or G or a small naturally or non-naturally occurring amino acid;

$X^7$ is absent or V or a hydrophobic or a small naturally or non-naturally occurring amino acid;

$X^8$ is absent or E or a hydrophobic or a small naturally or non-naturally occurring amino acid;

$X^9$ is absent or P or a basic or a polar naturally or non-naturally occurring amino acid;

$X^{10}$ is absent or D or an acidic or polar naturally or non-naturally occurring amino acid;

$X^{11}$ is absent or I or a hydrophobic naturally or non-naturally occurring amino acid;

$X^{12}$ is absent or G or a small naturally or non-naturally occurring amino acid;

$X^{13}$ is absent or Q or a polar or basic naturally or non-naturally occurring amino acid;

$X^{14}$ is absent or T or a polar naturally or non-naturally occurring amino acid;

$X^{15}$ is absent or Y or a polar or acidic naturally or non-naturally occurring amino acid;

$X^{16}$ is absent or F or hydrophobic or an aromatic naturally or non-naturally occurring amino acid;

$X^{17}$ is absent or E or a basic or a polar naturally or non-naturally occurring amino acid;

$X^{18}$ is absent or E or absent or a polar or acidic naturally or non-naturally occurring amino acid;

$X^{19}$ is absent or S or a polar naturally or non-naturally occurring amino acid;

$X^{20}$ is absent or R or a basic or polar naturally or non-naturally occurring amino acid;

$X^{21}$ is absent or I or a hydrophobic naturally or non-naturally occurring amino acid;

$X^{22}$ is absent or N or a polar or basic naturally or non-naturally occurring amino acid;

$X^{23}$ is absent or Q or a polar or basic naturally or non-naturally occurring amino acid;

$X^{24}$ is absent or D or a hydrophobic or a small naturally or non-naturally occurring amino acid; and $X^{25}$ is absent or a naturally or non-naturally occurring amino acid or a small peptide, or a pharmaceutically acceptable salt thereof.

In some embodiments, the astexin-1 peptide comprises the sequence GLSQGVEPDIGQTYFEESRINQD (SEQ ID NO:3).

In some embodiments, $X^1$ is MHTPIISTTVQPKT (SEQ ID NO:4).

In some embodiments, astexin-1 shows antimicrobial activity against *C. crescentus*.

An astexin-2 peptide of the invention includes a substantially purified peptide based on the following amino acid sequence:

$H_2N—Y^1—Y^2—Y^3—Y^4—Y^5—Y^6—Y^7—Y^8—Y^9—Y^{10}—Y^{11}—Y^{12}—Y^{13}—Y^{14}—Y^{15}—Y^{16}—Y^{17}—Y^{18}—Y^{19}—Y^{20}—Y^{21}—Y^{22}—Y^{23}—Y^{24}—COOH$, wherein

- $Y^1$ is absent or a peptide sequence or a naturally or non-naturally occurring amino acid;
- $Y^2$ is absent or G or a small naturally or non-naturally occurring amino acid;
- $Y^3$ is absent or L or a hydrophobic or a small naturally or non-naturally occurring amino acid;
- $Y^4$ is absent or T or a polar naturally or non-naturally occurring amino acid;
- $Y^5$ is absent or Q or a polar or acidic naturally or non-naturally occurring
- $Y^6$ is absent or I or a hydrophobic naturally or non-naturally occurring amino acid;
- $Y^7$ is absent or Q or a polar or acidic naturally or non-naturally occurring amino acid;
- $Y^8$ is absent or A or a hydrophobic or a small naturally or non-naturally occurring amino acid;
- $Y^9$ is absent or L or a hydrophobic or a small naturally or non-naturally occurring amino acid;
- $Y^{10}$ is absent or D or a hydrophobic or a small or an acidic naturally or non-naturally occurring amino acid;
- $Y^{11}$ is absent or S or a polar naturally or non-naturally occurring amino acid;
- $Y^{12}$ is absent or V or a hydrophobic naturally or non-naturally occurring amino acid;
- $Y^{13}$ is absent or S or a polar naturally or non-naturally occurring amino acid;
- $Y^{14}$ is absent or G or a small naturally or non-naturally occurring amino acid;
- $Y^{15}$ is absent or Q or a polar or acidic naturally or non-naturally occurring amino acid;
- $Y^{16}$ is absent or F or hydrophobic or an aromatic naturally or non-naturally occurring amino acid;
- $Y^{17}$ is absent or R or a basic or a polar naturally or non-naturally occurring amino acid;
- $Y^{18}$ is absent or D or absent or a polar or an acidic or a polar naturally or non-naturally occurring amino acid;
- $Y^{19}$ is absent or Q or basic or a polar naturally or non-naturally occurring amino acid;
- $Y^{20}$ is absent or L or a hydrophobic or a small naturally or non-naturally occurring amino acid;
- $Y^{21}$ is absent or G or a small naturally or non-naturally occurring amino acid;
- $Y^{22}$ is absent or L or a hydrophobic or a small naturally or non-naturally occurring amino acid;
- $Y^{23}$ is absent or S or a polar naturally or non-naturally occurring amino acid
- $Y^{24}$ is absent or A or a hydrophobic or a small naturally or non-naturally occurring amino acid;
- $Y^{25}$ is absent or D or a polar or an acidic or a polar naturally or non-naturally occurring amino acid.

In some embodiments, the Astexin-2 peptide comprises the sequence (SEQ ID NO: 5)
GLTQIQALDDSVSGQFRDQLGLSAD.

In some embodiments, $Y^1$ is MKRTTIAARRVGL-IDLGKATRQTK (SEQ ID NO:6).

An astexin-3 peptide of the invention is based on the following amino acid sequence:

$H_2N-Z^1-Z^2-Z^3-Z^4-Z^5-Z^6-Z^7-Z^8-Z^9-Z^{10}-Z^{11}-Z^{12}-Z^{13}-Z^{14}-Z^{15}-Z^{16}-Z^{17}-Z^{19}-Z^{20}-Z^{21}-Z^{22}-Z^{23}-Z^{24}-Z^{25}-Z^{26}-COOH$, wherein

- $Z^1$ is absent or a peptide sequence or a naturally or non-naturally occurring amino acid;
- $Z^2$ is absent or G or a small naturally or non-naturally occurring amino
- $Z^3$ is absent or P or a naturally or non-naturally occurring amino acid;
- $Z^4$ is absent or T or a polar naturally or non-naturally occurring amino acid;
- $Z^5$ is absent or P or a naturally or non-naturally occurring amino acid;
- $Z^6$ is absent or M or a hydrophobic naturally or non-naturally occurring amino acid;
- $Z^7$ is absent or V or a hydrophobic naturally or non-naturally occurring amino acid;
- $Z^8$ is absent or G or a small naturally or non-naturally occurring amino acid;
- $Z^9$ is absent or L or a hydrophobic naturally or non-naturally occurring amino acid;
- $Z^{10}$ is absent or D or a small or an acidic naturally or non-naturally occurring amino acid;
- $Z^{11}$ is absent of S or a small or polar naturally or non-naturally occurring amino acid;
- $Z^{12}$ is absent or V or a hydrophobic naturally or non-naturally occurring amino acid;
- $Z^{13}$ is absent or S or a small or polar naturally or non-naturally occurring amino acid;
- $Z^{14}$ is absent or G or a small naturally or non-naturally occurring amino acid;
- $Z^{15}$ is absent or Q or a basic or a polar naturally or non-naturally occurring amino acid;
- $Z^{16}$ is absent or Y or a hydrophobic or an aromatic naturally or non-naturally occurring amino acid;
- $Z^{17}$ is absent or W or a hydrophobic or an aromatic naturally or non-naturally occurring amino acid;
- $Z^{18}$ is absent or D or a small or an acidic naturally or non-naturally occurring amino acid;
- $Z^{19}$ is absent or Q or a basic or a polar naturally or non-naturally occurring amino acid;
- $Z^{20}$ is absent or H or a basic or polar naturally or non-naturally occurring amino acid;
- $Z^{21}$ is absent or A or a small hydrophobic naturally or non-naturally occurring amino acid;
- $Z^{22}$ is absent or P or a naturally or non-naturally occurring amino acid;
- $Z^{23}$ is absent or L or a hydrophobic naturally or non-naturally occurring amino acid;
- $Z^{24}$ is absent or A or a small or hydrophobic naturally or non-naturally occurring amino acid;
- $Z^{25}$ is absent or D or a polar or acidic naturally or non-naturally occurring amino acid; and
- $Z^{26}$ is absent or a peptide or a polar or acidic naturally or non-naturally occurring amino acid.

In some embodiments, the Astexin-3 peptide comprises the amino acid sequence (SEQ ID NO: 7)
GPTPMVGLDSVSGQYWDQHAPLAD.

In some embodiments, $Z^1$ is MRTYNRSL-PARAGLTDLGKVTTHTK (SEQ ID NO:8).

In some embodiments, the Astexin-3 peptide is provided as a lasooed peptide, e.g, the G at $Z^2$ in the Astexin-3 peptide is covalently bound to D at $Z^{10}$.

The astexin peptides of the invention are additionally useful as, e.g. receptor antagonists, enzyme inhibitors, and as inhibitors of viral fusion. The peptides of the invention can also be used in peptide therapeutics, as molecular sensors for disease diagnostics, and as molecular probes for biochemical research.

In some embodiments, the astexin peptide is less than 50 amino acids, e.g., less than 35 amino acids, less than 30 amino acids, or less than 25 amino acids.

By a substantially pure peptide or polypeptide is meant a peptide or polypeptide that is separated from those components (e.g., the proteins and other naturally-occurring organic molecules) which naturally accompany it. A polypeptide is substantially pure when it constitutes at least 60%, by weight, of the protein in the preparation. Preferably, the protein in the preparation is at least 75%, more preferably at least 90%, and most preferably at least 99%, by weight, of the desired peptide. A substantially pure polypeptide is obtained, e.g., by extraction from a natural source; by expression of a recombinant nucleic acid; or by chemically synthesizing the protein. Purity is measured by a number appropriate methods known in the art, e.g., column chromatography, polyacrylamide gel electrophoresis, or HPLC analysis. A protein is substantially free of naturally associated components when it is separated from those contaminants which accompany it in its natural state. Thus, a protein which is chemically synthesized or produced in a cellular system different from the cell from which it naturally originates is substantially free from its naturally associated components.

In some embodiments, the astexin peptide is a substrate for an isopeptidase, e.g., an AtxE2 isopeptidase.

In some embodiments, the peptide is isolated from a cell that contains a naturally occurring astexin peptide.

In some embodiments, the peptide is isolated from an astexin peptide recombinantly produced in a cell. The cell can be, e.g., a prokaryotic cell or a eukaryotic cell.

In some embodiments, the astexin peptide is chemically synthesized in vitro.

The term "consisting essentially of", and variants thereof, when used, to refer to the position, are used herein to mean that the composition includes a sole active peptide and other desired pharmaceutically inactive additives excipients, and/or components (e.g., polymers, sterically hindered primary amines, cations, filling agents, binders, carriers, excipients, diluents, disintegrating additives, lubricants, solvents, dispersants, coating additives, absorption promoting additives, controlled release additives, anti-caking additives, anti-microbial additives, preservatives, sweetening additives, colorants, flavors, desiccants, plasticizers, dyes, or the like), and no other active pharmaceutical ingredient(s).

In another aspect, the invention provides a non-naturally occurring polynucleotide sequence encoding an astexin peptide.

Also provided by the invention is a vector comprising polynucleotide encoding an astexin peptide. Also provided by the invention is cell containing the vector. The cell can be, e.g., a prokaryotic cell such as an *Escherichia coli* cell or an *Asticcacaulis excentricus* cell.

Also provided by the invention is an astexin library comprising a plurality of vectors encoding an astexin peptide. The vectors include an insertion of one to five codons of a polynucleotide sequence encoding a non-astexin peptide.

In some embodiments, the insertion is in a loop or ring of the astexin peptide. In some embodiments, the insertion is 3-4 codons of a polypeptide-encoding region of the polynucleotide.

Also provided by the invention is a method of expressing a peptide, the method comprising culturing the cell containing an astexin-encoding polynucleotide under conditions allowing for expression of the astexin peptide. The method optionally includes recovering the astexin peptide.

Also included in the invention is a method of removing a toxic substance from a sample suspected of containing the toxic substance. The method includes contacting the sample with an astexin peptide under conditions that allow for formation of a complex between the toxic substance and the peptide and removing the complex from the sample to remove the toxic substance from the sample. The sample can be, e.g., a soil sample or a water sample. The toxic substance can be, e.g., a metal such as cadmium or lead.

In another aspect the invention provides a method of inhibiting the growth of a microbe by contacting the microbe with an astexin peptide in an amount sufficient to inhibit growth of the microbe. In some embodiments, the astexin peptide binds heavy metals in an amount sufficient to inhibit growth of the microbe. The microbe can be, e.g., a prokaryote or a eukaryote.

In another aspect, the invention provides a method of purifying a protein, the method comprising heating a solution containing an astexin fusion protein, the fusion protein comprising an astexin peptide and a second protein moiety, centrifuging the heated solution and recovering the astexin-peptide containing fusion protein. The fusion protein is then cleaved with a lasso protease to separate the astexin peptide and the second protein moiety, and the second protein moiety is isolated, thereby purifying the protein.

Also provided by the invention is a substantially purified AtxE2 polypeptide at least 85% identical to the ATEX2 polypeptide sequence of SEQ ID NO:1. In some embodiments, the polypeptide s at least 90%, 95%, 98% or 99% or more identical to the ATEX2 polypeptide sequence. In some embodiments, the polypeptide includes a catalytic serine residue at position 527 when numbered with respect to the corresponding ATEX2 polypeptide sequence.

Also within the invention is a non-naturally occurring polynucleotide sequence encoding an astexin peptide.

In a further aspect, the invention provides a method of regulating expression or activity of an astexin peptide. The method comprises providing a cell containing (1) a polynucleotide encoding an astexin peptide and (2) a polynucleotide encoding an AtxE2 polypeptide; culturing the cell under conditions allowing for expression of the Astexin-2 polypeptide and second moiety, and inducing expression of an AtxE2 polypeptide under conditions that cause hydrolysis of the astexin-2 peptide, thereby regulating expression or activity of the astexin peptide.

In some embodiments, the astexin-2 encoding polynucleotide is operably linked to a second moiety.

In some embodiments, the second moiety is a polypeptide or a label.

In some embodiments, the cell does not naturally express an astexin peptide or an AtxE2 peptide.

In some embodiments, the astexin-encoding polynucleotide and AtxE2 encoding polynucleotide are covalently linked.

In some embodiments, the astexin-2 encoding polynucleotide and AtxE2-encoding polynucleotide are not covalently linked, i.e., they are on separate polynucleotides.

Peptides within the invention can be produced using methods known in the art, e.g., by purifying the peptide sequence from a naturally occurring protein or peptide. Purification can be performed along with a cleavage or degradation (either enzymatic or non-enzymatic) to produce the desired peptide using methods known the art.

Alternatively, products can be biochemically synthesized using, e.g., solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence).

Solid phase polypeptide synthesis procedures are well known in the art and further described by John Morrow Stewart and Janis Dillaha Young, Solid Phase Peptide Syntheses (2nd Ed., Pierce Chemical Company, 1984). Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Polypeptides or peptides can alternatively be synthesized using recombinant techniques such as those described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Also within the invention are variant forms of astexin peptides in which new/unnatural functionality has been introduced into a naturally-encoded astexin peptide. By "variant" is meant a peptide that differs from a reference peptide, but retains essential properties of the reference peptide. Generally, differences are such that the sequences of the reference peptide and the variant are closely similar overall and, in many regions, identical.

A variant and reference peptide may differ in amino acid sequence by one or more substitutions, additions, and/or deletions, in any combination. A substituted or inserted amino acid residue may or may not be one encoded by the genetic code. A variant of a peptide or polypeptide may be a naturally occurring such as an allelic variant, or it may be a variant that is not known to occur naturally. Non-naturally occurring variants of polypeptides may be made by mutagenesis techniques or by direct synthesis.

Generally, the variant differs from the reference polypeptide by conservative amino acid substitutions, whereby a residue is substituted by another with like characteristics (e.g. acidic, basic, aromatic, etc.). Typical substitutions are among Ala, Val, Leu and Ile; among Ser and Thr; among the acidic residues Asp and Glu; among Asn and Gln; and among the basic residues Lys and Arg; or aromatic residues Phe and Tyr.

A peptide within the invention may include one or more modifications. For example, it may be provided phosphorylated (typically at a serine, threonine, or tyrosine residue), pegylated, coupled to a biotin moiety, or include a disulfide bond to another peptide, polypeptide or amino acid. The peptide may be provided in a cyclic form, e.g., as a cyclic peptide or as a lactam. Alternatively, or in addition, the peptide may be provided as a branched peptide. These cyclic and branched forms can be in addition to the lasso peptide structures described herein.

The peptide may be additionally modified (when linear) at its amino terminus or carboxy terminus. Examples of amino terminal modifications include, e.g., an N-glycated, N-alkylated, N-acetylated or N-acylated amino acid. A terminal modification can include a pegylation. An example of a carboxy terminal modification is a c-terminal amidated amino acid.

A peptide of the invention may contain amino acids other than the 20 gene-encoded amino acids. When amino acids are not designated as either D- or L-amino acids, the amino acid is either an L-amino acid or could be either a D- or L-amino acid, unless the context requires a particular isomer.

The notations used herein for the polypeptide amino acid residues are those abbreviations commonly used in the art. The less common abbreviations Abu, Cpa, Nle, Pal, Tle, Dip, 4-Fpa, and Nal stand for 2-amino-butyric acid, p-chlorophenylalanine, norleucine, 3-pyridyl-2-alanine, tert-leucine, 2,2-diphenylalanine, 4-fluoro-phenylalanine, and 3-(2-naphthyl)-alanine or 3-(1-naphthyl)-alanine, respectively.

One example of a non-naturally occurring amino acid is an omega-amino acid, e.g., β-alanine (β-Ala), or 3 aminopropionic (3-aP). Other examples are non-naturally occurring amino acids, e.g., sarcosine (Sar), β-alanine (β-Ala), 2,3 diaminopropionic (2,3-diaP) or alpha-aminisobutyric acid (Aib); omega-acid is beta-alanine (beta-Ala), or 3 aminopropionic (3-aP); a hydrophobic non-naturally occurring amino acid, such as t-butylalanine (t BuA), t butylglycine (t BuG), N methylisoleucine (N MeIle), norleucine (Nle), methylvaline (Mvl), cyclohexylalanine (Cha), phenylglycine (Phg), NaI, β2-thienylalanine (Thi), 2 naphthylalanine (2 NaI), or 1,2,3,4-tetrahydroisoquinoline-3 carboxylic acid (Tic); a basic amino acid, such as ornithine (Orn) or homoarginine (Har); and a neutral/polar non-naturally occurring amino acid is citrulline (Cit), Acetyl Lys, or methionine sulfoxide (MSO).

Non-conventional amino acids are also listed below:

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| Cyclohexylalanine | Chexa | L-N-methylhistidine | Nmhis |
| Cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |

-continued

| Non-conventional amino acid | Code | Non-conventional amino acid | Code |
|---|---|---|---|
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclo-hexylalanine | Mchexa |
| D-α-methylarginine | Dmarg | α-methylcyclo-pentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Ngiu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngin |
| D-α-methylornithine | Dmorn | N-(carbamylmethyl)glycine | Nasn |
| D-α-methylphenylalanine | Dmphe | N-(2-carboxyethyl)glycine | Ngiu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptohan | Dmtrp | N-cyclohexylglycine | Nchex |
| D-α-methyltyrosine | Dmty | N-cyclodecylglycine | Ncdec |
| D-α-methylvaline | Drnval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |

| Non-conventional amino acid | Code | Non-conventional amino acid | Code |
|---|---|---|---|
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
| | nbhm | | |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenylhylamino)cyclopropane | Nmbc | | |

If a peptide according to the present invention is a linear molecule, it is possible to place various functional groups at various points on the linear molecule that are susceptible to or suitable for chemical modification. Functional groups can be added to the termini of linear forms of the peptide. In some embodiments, the functional groups improve the activity of the peptide with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are optionally independently an aliphatic, substituted aliphatic, benzyl, substituted benzyl, aryl or a substituted aryl group. In addition, taken together with the nitrogen atom, R$_2$ and Rican optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH$_2$, —NHCH$_2$, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH$_3$, —O-(ethyl), —O-(n- propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native peptide protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S, 3R)-methyl-phenylalanine, (2R,3S)-methyl-phenylalanine and (2R,3R)-methyl-phenylalanine (Kazmierski and Hruby, Tetrahedron Lett. (1991)).

Exemplary, non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA), for example.

Chemical Modifications

Any part of a peptide within the invention may optionally be chemically modified, i.e. changed by addition of functional groups. For example, the side amino acid residues appearing in the native sequence may optionally be modified, although as described below alternatively other part(s) of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a peptide, as described in PCT Application No. WO 2006/050262, hereby incorporated by reference as if fully set forth herein. These moieties are designed for use with biomolecules and may optionally be used to impart various properties to proteins.

Furthermore, optionally any point on a peptide may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Covalent modifications of the peptides of the present invention are included within the scope of this invention. Other types of covalent modifications of the peptides are introduced into the molecule by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl)carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking CHF to a water-insoluble support matrix or surface for use in the method for purifying anti-CHF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983]), acetylation of the N-terminal amine, and amidation of any C-terminal carboxyl group.

Astexin1, Astexin2, Astexin 3, and AtxE2 Nucleic Acids

A polynucleotide encoding an astexin or AtexE2 peptide according to the invention is preferably a non-naturally occurring nucleic acid. Non-naturally occurring as applied to an object means that the object cannot be found in nature as distinct from being artificially produced by man. "Naturally occurring" as applied to an object refers to the fact that the object can be found in nature as distinct from being artificially produced by man. A polypeptide or polynucleotide sequence that is present in an organism (including viruses, bacteria, protozoa, insects, plants or mammalian tissue) that can be isolated from a source in nature and which has not been intentionally modified by man in the laboratory is naturally occurring.

In some embodiments, a polynucleotide according to the invention is within 100 kilobases of the 5' and/or 3' terminus of a linear polynucleotide. For example, in various embodiments the polynucleotide is within 50 kb, 25 kb, 10 kb, 1 kb, 500 nucleotides, 250 nucleotides, 125 nucleotides, 50 nucleotides, or 1-5 nucleotides of a 5' or 3' terminus.

Astexin and/or AtxE2 peptides and polypeptides can be expressed using a nucleic acid construct which includes at least an astexin or AtxE2 nucleic acid sequence. The nucleic acid construct optionally includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto. Any suitable promoter sequence can be used by the nucleic acid construct of the present invention. Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

The nucleic acid transfer techniques can include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining elements, or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptides of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Recombinant Astexin, and AtxE2 Vectors and Host Cells

Another aspect of the invention pertains to vectors, preferably expression vectors, containing a nucleic acid encoding a protein of the invention, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequences in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, Gene Expression Technology Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for production of variant proteins in prokaryotic or eukaryotic cells. For example, proteins of the invention can be expressed in bacterial cells such as *Escherichia coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., Gene Expression Technology: Methods in Enzymology 185, Academic Press, San Diego, Calif. (1990) 60-89)—not accurate, pET11a-d have N terminal T7 tag.

One strategy to maximize recombinant protein expression in *E. coli* is to express the protein in a host bacterium with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

In another embodiment, the expression vector encoding for the protein of the invention is a yeast expression vector. Examples of vectors for expression in yeast *Saccharomyces cerevisiae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, polypeptides of the present invention can be produced in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to mRNA encoding for protein of the invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, protein of the invention can be produced in bacterial cells such as *E. coli*, insect cells, yeast, plant or mammalian cells (such as Chinese hamster ovary cells (CHO) or COS or 293 cells). Other suitable host cells are known to those skilled in the art.

DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

For efficient production of the protein, it is preferable to place the nucleotide sequences encoding the protein of the invention under the control of expression control sequences optimized for expression in a desired host. For example, the sequences may include optimized transcriptional and/or translational regulatory sequences (such as altered Kozak sequences).

The invention is further illustrated in the following non-limiting examples.

Example 1. Cloning and Heterologous Expression of Astexins-2 and -3

Lasso peptides can typically be expressed in greater yield using *E. coli* as a heterologous host than the native organism in which the combined effects of regulatory elements and weak natural promoters can make isolation of these natural products impractical[4-6,12,13]. We made three constructs for the expression of astexins-2 and -3 (FIG. 2). In the plasmid pMM37, the natural astexin-2, -3 cluster is placed under the control of the strong tet promoter[14]. Both precursors include a ribosome binding sequence upstream of their respective genes. Inverted repeat (hairpin) sequences are located downstream of each precursor (hairpins 1 and 3) with an additional smaller hairpin (hairpin 2) appearing before the second precursor (FIG. 2). We removed the astexin-2 precursor from pMM37 to express astexin-3 on its own (pMM39).

To express only astexin-2, we excised the astexin-3 precursor and the intergenic region between the two precursors from pMM37 by overlap PCR to give pMM40. As a consequence, both pMM40 and pMM39 have the same intergenic region between the precursor and the maturation enzymes. A fourth control construct, containing only the maturation enzymes, was constructed and named pMM38.

We expressed all four constructs in 20 amino acid M9 media at various scales with induction at $OD_{600}$=0.2-0.3. We then extracted the supernatants and boiled cell lysates and tested the crude extracts for the presence of astexins-2 and -3 by HPLC and MALDI mass spectrometry (MS) (see Online Methods). There are several peaks in the HPLC chromatograms of pMM37, pMM39 and pMM40 lysates that are not present in the control (FIG. 3). MS spectra of the extracts confirm the presence of C-terminal truncations of astexin-2 in cells harboring pMM37 and pMM40 as well as full-length and C-terminal truncations of astexin-3 in pMM39. As expected, each astexin species is singly dehydrated suggesting the presence of an isopeptide bond.

To assign astexin-2, astexin-3 and their truncation variants to individual peaks in the chromatogram, we analyzed the material collected from the 14.64, 15.09, 15.45, 12.24, and 14.14 min peaks by MALDI MS. Only small amounts of astexin-2 and astexin-3 species were detected in culture supernatants indicating that these peptides are not exported into the extracellular medium.

The combined results indicate that full-length astexin-3 and its ΔC2 and ΔC1 C-terminal truncation products are expressed from pMM39, while pMM40 expression yields mostly ΔC4 and ΔC3 truncations of astexin-2 with essentially no full-length product. The HPLC trace of the pMM37 extract shows that both astexin-2 and astexin-3 are present in the lysate, but the MALDI signal is dominated by astexin-2. This can be explained by preferential ionization of the arginine-containing astexin-2 in positive ion mode. Similar amounts of astexin-2 are produced by cells harboring the dual precursor construct pMM37 and the single precursor construct pMM40. In contrast, cells with the single precursor construct pMM39 produce ca. 4-fold more astexin-3 than do cells harboring pMM37 (FIG. 3). These results suggest that hairpin 3 (FIG. 2) does not prevent lasso peptide production, a result that is in contrast to what was observed for astexin-1 where removal of the hairpin led to improved production[4]. Non-specific cellular proteases are likely responsible for generating C-terminal truncations of astexins-2 and -3, and this process appears to be time dependent for astexin-3. After 48 hours of expression, a lysate extract of pMM39 contained mostly ΔC2 astexin-3 (55% of total product), but full-length astexin-3 was still the major product after 12 hours of expression (81%). Finally, we have observed oxidation of Met5 in astexin-3 to methionine sulfoxide after prolonged incubation in methanol while exposed to the atmosphere.

Two additional peaks are present in the pMM40 chromatogram at 15.48 and 16.95 min. MALDI MS analysis of HPLC collected fractions showed that these have the same molecular mass as astexin-2 ΔC4 and ΔC3, respectively. It has previously been observed that in certain lasso peptides, the tail can escape the confines of the ring at high temperatures[6,13] thus "unthreading" the lasso. Since our purification method includes a boiling step, these species are likely unthreaded variants of astexin-2. We tested this hypothesis by incubating an extract of pMM40 at 98° C. for two hours followed by centrifugation to remove precipitates. The main peaks for astexin-2 ΔC4 and ΔC3 at 12.24 and 14.14 min were gone after the thermal treatment, but the 15.48 and 16.95 min peaks remained and were even enriched. In contrast, unthreading of astexin-3 was not observed after heating for 3 hours at 95° C.

Example 2. Mass Spectrometric Analysis of Astexin-2 and -3

We carried out extensive mass-spectrometric studies on both astexin-2 and astexin-3 to confirm their identity and sequence composition. The internal cyclization in lasso peptides produces a distinct $MS^2$ fingerprint[15-17]. Specifically, while the macrolactam ring stays intact, the full y- and b-series of fragment ions are usually generated from residues in the loop and the tail. Astexins-2 and -3 have only one possible point of cyclization at Asp9. To confirm this, we subjected astexins-2 ΔC3, astexin-3 and synthetic linear versions of these peptides to $MS^2$ fragmentation. The ratios of fragment ions in the $MS^2$ spectra of the lassoed and synthetic linear peptides are strikingly different. Furthermore, the smallest observed b-series fragment (b9) and the largest observed y-series fragment (y15) of astexin-3 correspond to only the ring and only the tail respectively. This indicates that the point of cyclization is indeed between Gly1 and Asp9. Conversely, strong signals for y21 and y18 fragment ions were observed in the $MS^2$ spectrum of the linear astexin-3, which are indicative of fragmentation beyond Asp9. Similarly, the cyclization of astexin-2 ΔC3 at Asp9 was confirmed by the fact that the y-series of fragment ions terminates at y12 in the $MS^2$ spectrum. On the other hand, the $MS^2$ spectrum of the synthetic linear astexin-2 ΔC3 peptide has y-series fragment ions that include Gln4 through Leu8.

Example 3. NMR Solution Structure of Astexin-3

Samples of lassoed (3.25 mg) and synthetic linear (1.5 mg) astexin-3 were prepared in 200 μL DMSO-d6 each for the acquisition of TOCSY, NOESY and phase-sensitive COSY spectra on a Bruker Avance III 500 MHz spectrometer. In contrast to the extensive NOESY connectivity of the lassoed astexin-3, we did not detect significant NOESY cross peaks in the spectrum of the synthetic linear astexin-3. The TOCSY spectra of both the linear and lassoed astexin-3 have well defined signals, yet their observed distribution is markedly different. As previously noted for McjJ25[15] and other lasso peptides[18], the band of NH-Hα resonances is narrower in the f2 dimension in the synthetic linear astexin-3 than it is in the lassoed astexin-3.

We assigned all proton chemical shifts in the TOCSY and NOESY spectra of lassoed astexin-3 except the amide protons of Leu8 and Gln14. Chemical shifts of side chain protons of Leu8 were assigned based on cross peaks with its Hα proton and intra-residue resonances further up the sidechain. Similarly, we identified cross peaks corresponding to magnetization transfer between side chain protons of Gln14 and its Hα proton. Gln14 has a very strong resonance between its Hε protons in both the TOCSY and NOESY spectrum. While the NH-Hα cross peak for Tyr15 was weak in the TOCSY, the cross peak between the amide proton and the protons on the aromatic ring was strong. Trp16 and Tyr15 had extensive connectivity to residues in the ring of astexin-3. This evidence places the Tyr15/Trp16 dyad as the steric lock that traps the tail of astexin-3 in the ring. Specifically, we observed nineteen long-range NOE contacts between Trp16 and Met5, Thr3, Gly7, Asp9, Gly1, and Leu8. Tyr15 had four connections to residues in the ring. Additionally, we observed four contacts between side-chain protons of Gln14, the residue immediately preceding the steric lock, and protons in Leu8 and Val6, which are in the ring. Finally the presence of NOE contacts peaks between the NH proton of Gly1 and the Hβ protons of Asp9 confirmed the presence of the internal macrocycle.

The volumes of 120 inter-residue and 98 intra-residue cross peaks from the 100 ms NOESY spectrum were measured by integration and calibrated to the Gln14 Hε21-Hε22 crosspeak, yielding a set of upper distance restraints. Restrains on eleven φ torsion angles were derived from the vicinal coupling constants $^3J_{HN_\alpha}$. Proper geometry of the Gly1-Asp9 covalent linkage was realized by introducing 8 additional constraints. Based on structures generated in the first round of simulated annealing with CYANA 2.1[19], constraints that were violated in more than 10 of the 25 lowest energy structures were refined until the weighted sum of the squared violations of conformational restraints (CYANA target function) fell below 20 Å$^2$. Final simulated annealing was done from an initial set of 200 random structures and yielded an ensemble of top 20 structures with good covalent geometry and an average root-means-square (rms) deviation of 0.94±0.70 Å. These structures were subsequently energy minimized using TINKER[20] with the AMBER 94[21] force field to an rms gradient of 1.0 kcal/mole/Å.

Figure 4A:
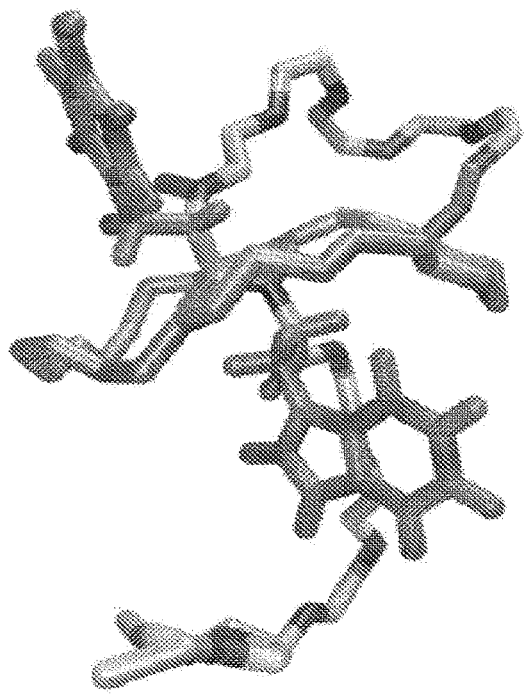
FIG. 4A-B: Representative solution structure of astexin-3. A: Lowest energy structure from the NMR ensemble. The steric lock residues Tyr15 and Trp16 prevent the tail of the peptide from slipping from the ring and are highlighted in red. B: Superposition of top 20 structures showing the low rms deviation of the ensemble of structures.
Figure 4B:
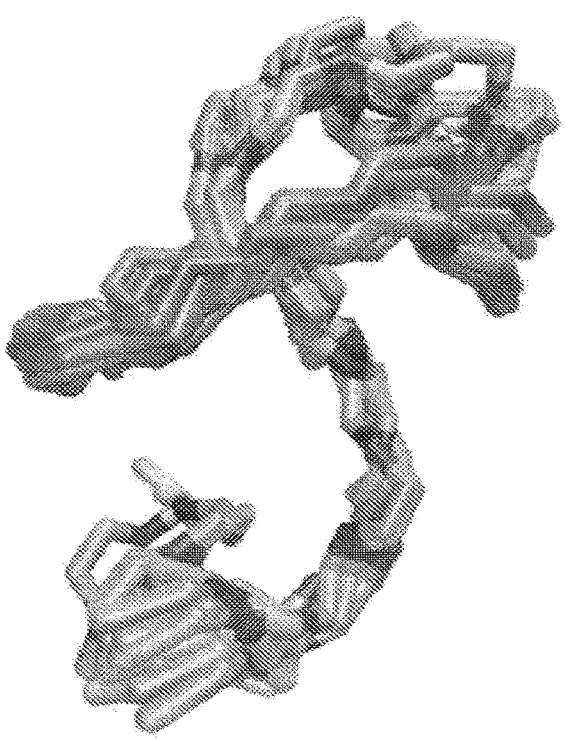

The structure of astexin-3 is presented in FIG. 4. The topology of astexin-3 features a relatively short six-residue loop and a nine-residue tail. The ring of the peptide is rigid, but there is some flexibility in the loop and in the tail. Most structural flexibility in the tail happens after His19 where it bends towards the ring. Observed long-range NOE contacts between His19, Ala20, Leu22, Asp24 and residues in the ring support this structural feature and suggest a compacting of the structure by minimization of solvent exposed area.

Example 4. AtxE2 is an Isopeptide Hydrolase of Astexins-2 and -3

Figure 5A:
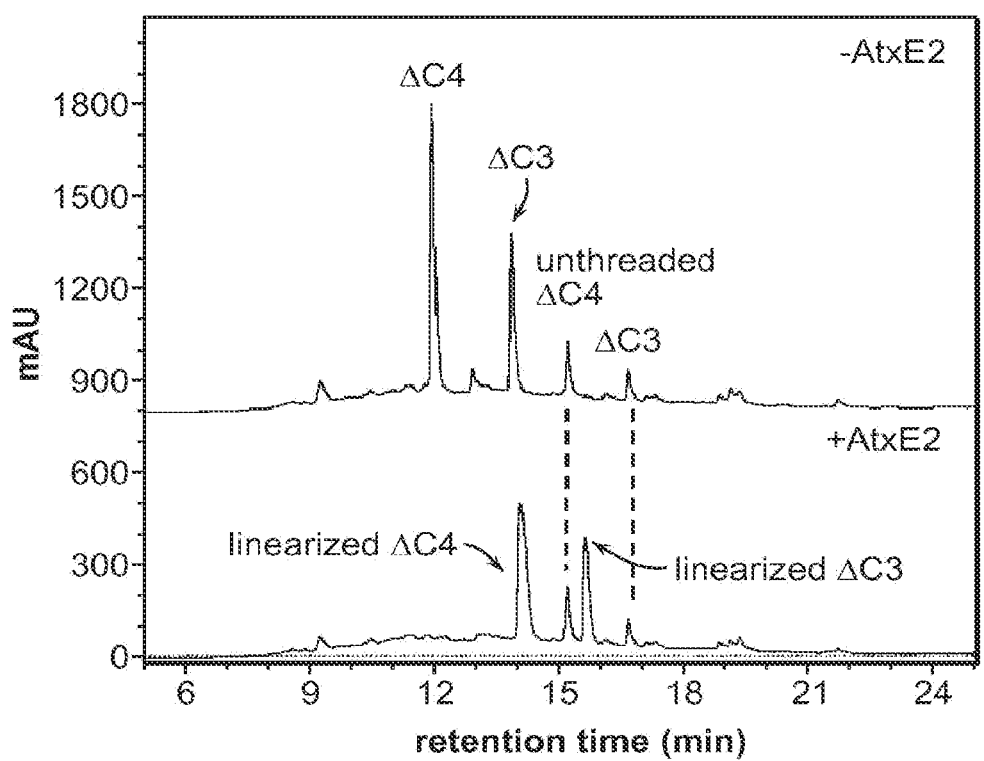

After producing astexins-2 and -3 and solving the astexin-3 structure, we turned our attention to the putative protease in this cluster, AtxE2. Given the low soluble yields and challenges in obtaining pure lasso peptide maturation enzymes[10,22], we were pleasantly surprised to note that a histidine-tagged AtxE2 expressed well and was readily purified to homogeneity. We investigated whether this enzyme had any activity towards astexins-2 and -3. To this end, we prepared pMM39 and pMM40 lysate extracts containing astexin-2 and astexin-3 and their C-terminal truncation variants (refer to FIG. 3). Since most of the cellular proteins and lipids are removed from the lysates prior to C8 extraction by boiling and centrifugation, thermostable lasso peptides are the major products in the extract without additional purification. We incubated 10 μL of each extract in a phosphate buffered saline solution at pH 7.5 with 860 nM AtxE2 for 6 hours at room temperature. The reaction mixture was then quenched by heating to 65° C. for 30 min and cleaned up for HPLC analysis. All astexin-2 species experienced an increase in retention time after AtxE2 treatment, while the retention time of the astexin-3 species decreased (FIG. 5A, 5C).

Figure 5B:
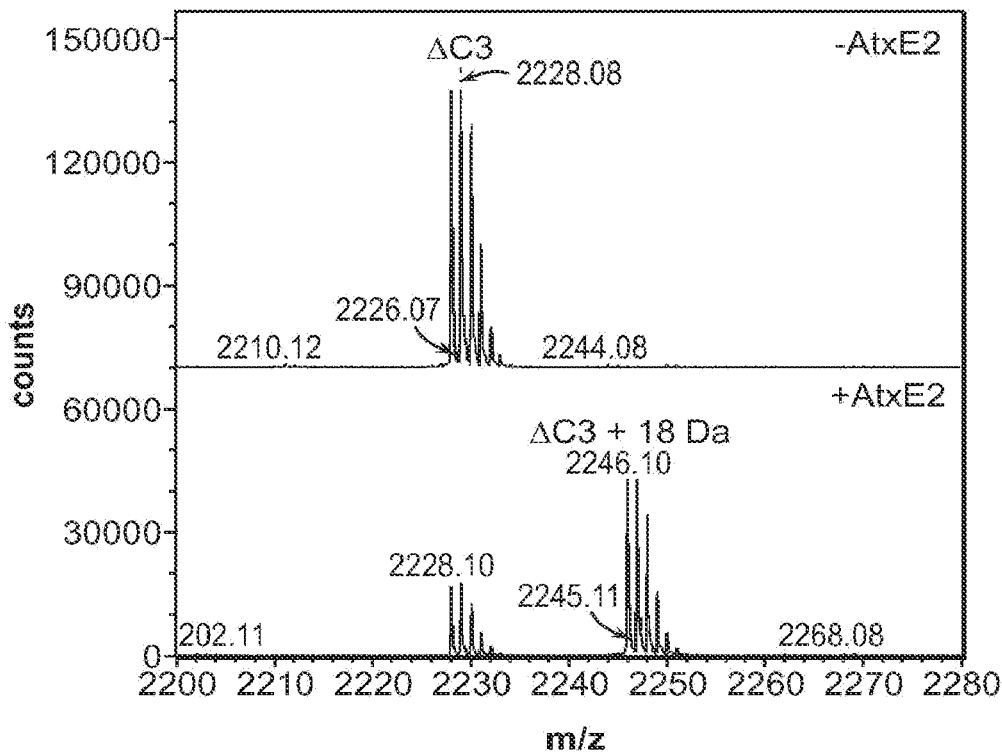
Figure 6A:
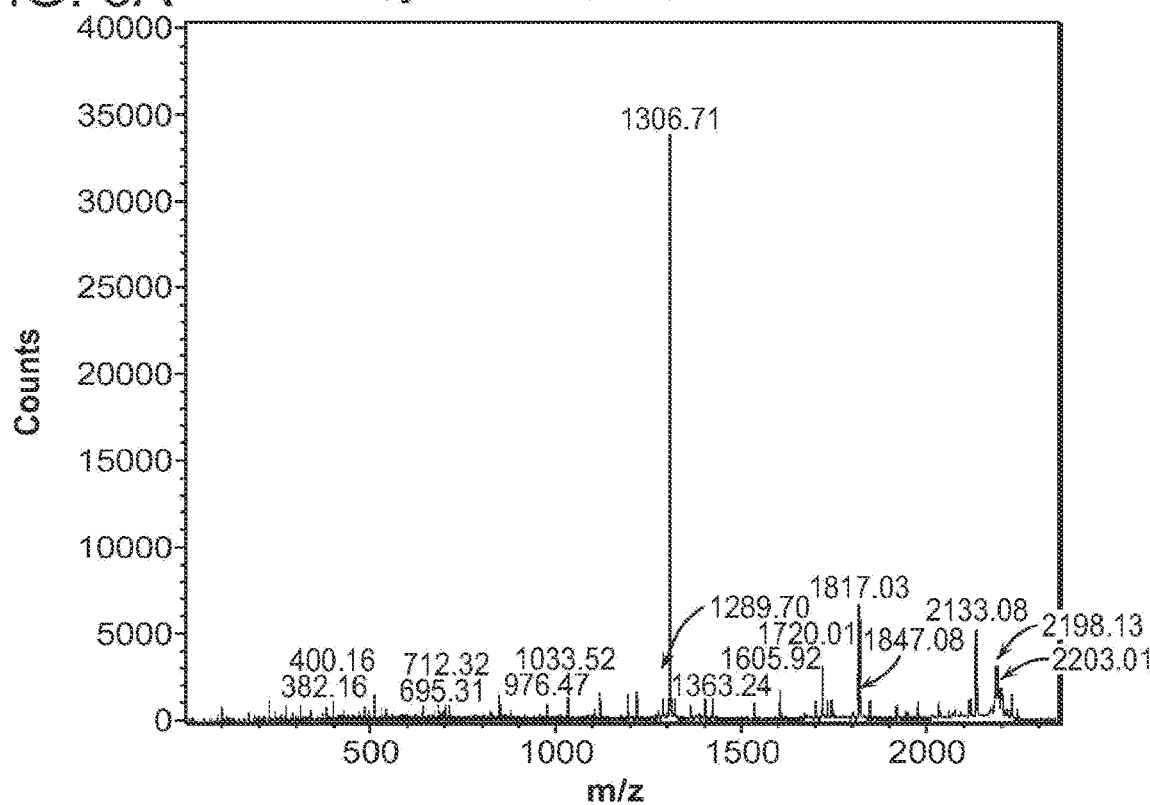
FIG. 6A-D: $MS^2$ analysis showing that the synthetic linear astexin-2 ΔC3 (A) is identical to the AtxE2 linearized astexin-2 ΔC3 (C) and that synthetic linear astexin-3 (B) is identical to AtxE2 linearized astexin-3 (D).
Figure 6B:
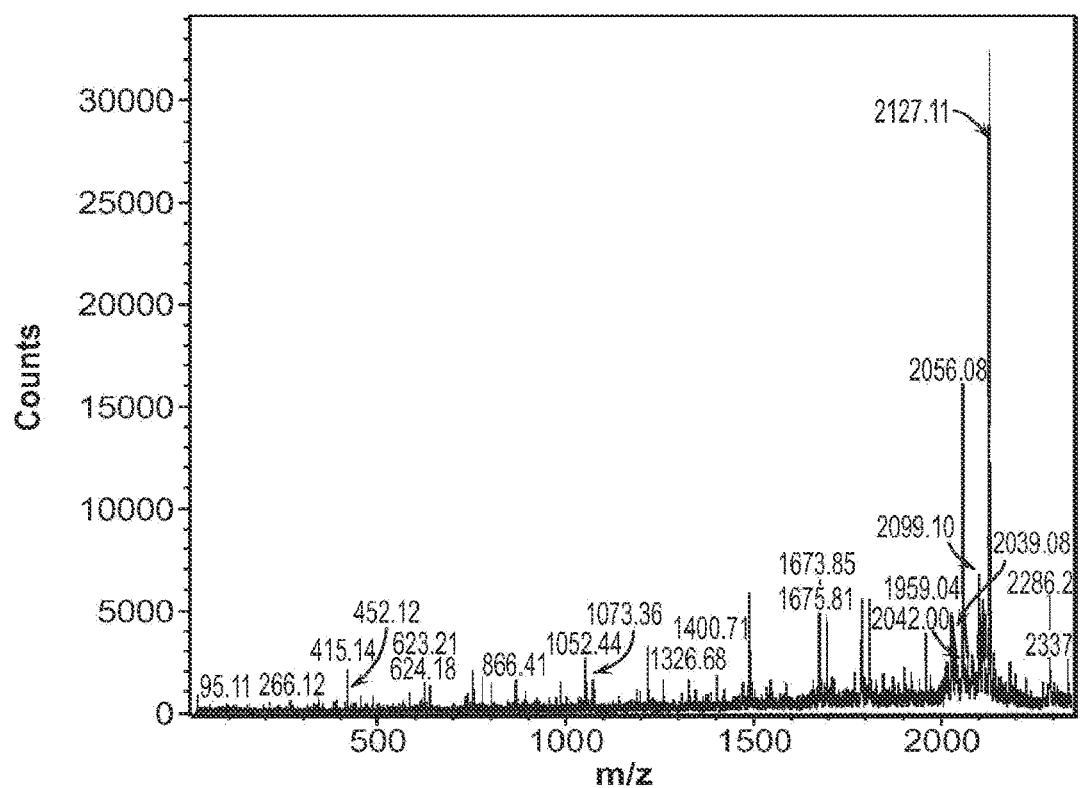
Figure 6C:
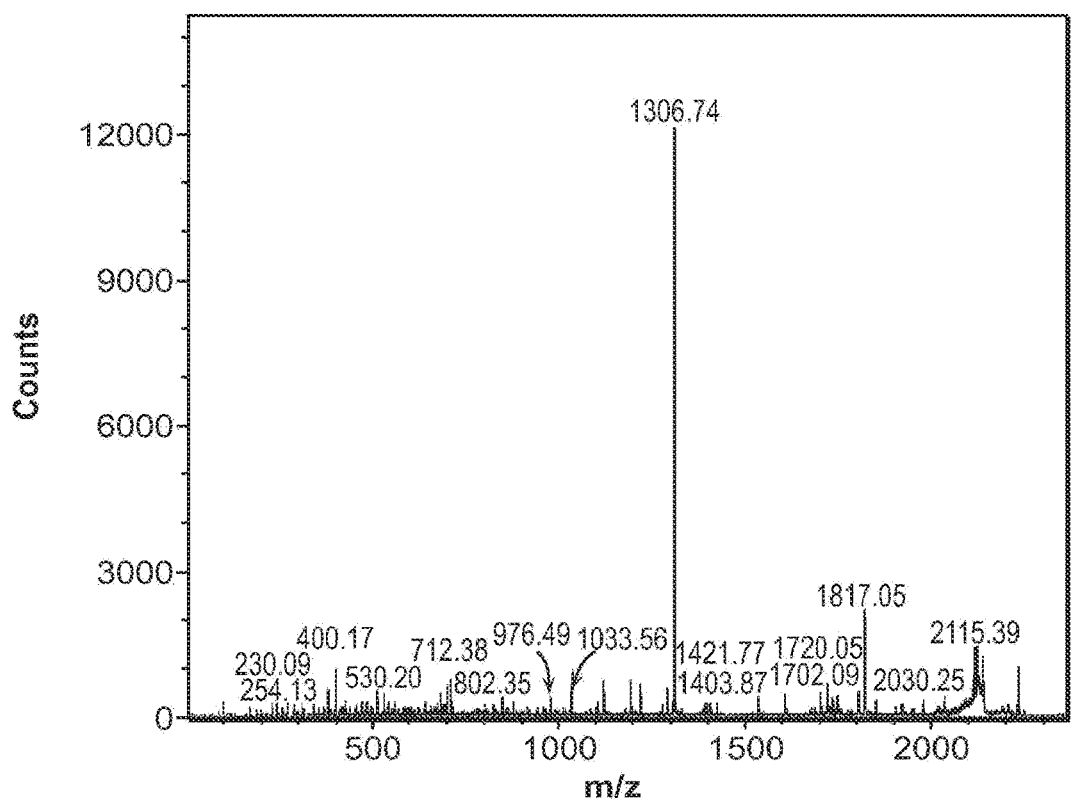
Figure 6D:
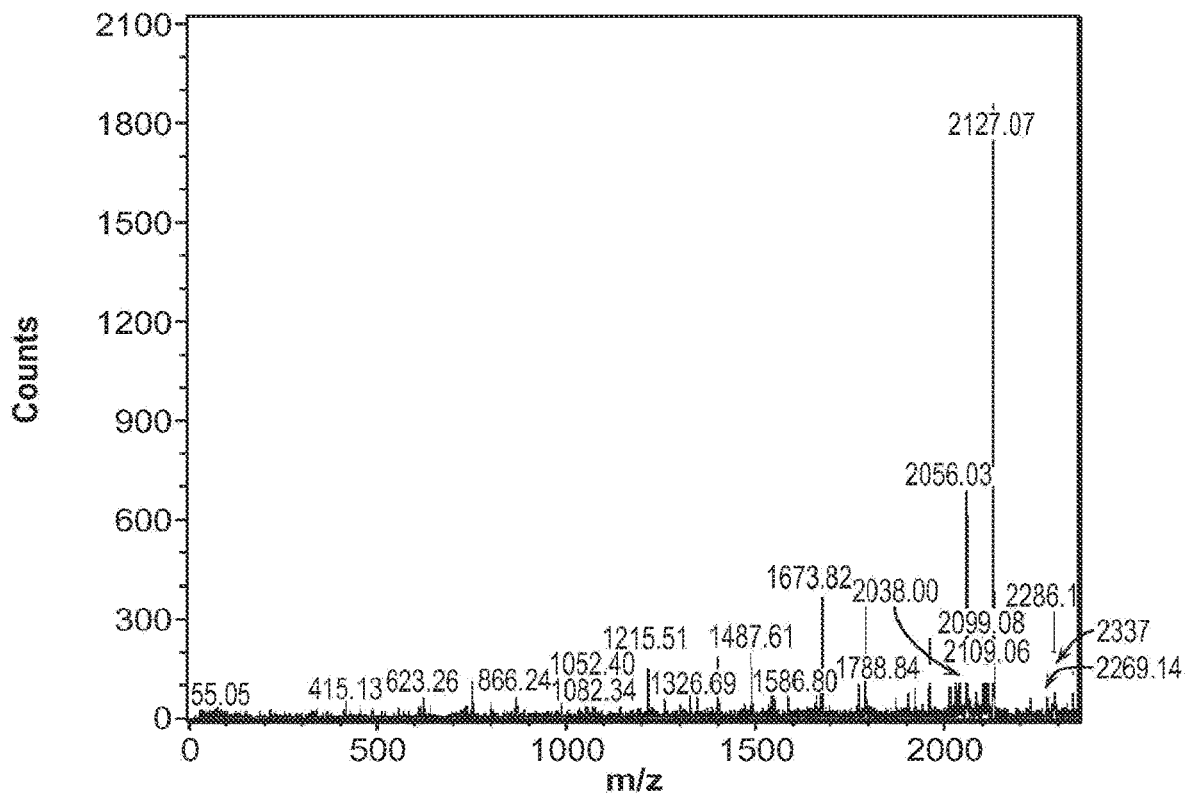

MALDI MS analysis of the reaction mixtures showed an increase of 18 mass units for all astexin-2 and astexin-3 species, corresponding to the addition of a water molecule via the cleavage of a single amide bond (FIG. 5B, 5D). Since the tail of astexin-3 is locked in place on either side of the ring by a tyrosine and a tryptophan residue, it is conceivable that one of the peptide bonds in the ring or the loop of the peptide could have been cut. However the $MS^2$ spectra of the linear synthetic astexin-2 and -3 peptides and the lasso peptides treated with AtxE2 are identical (FIG. 6). This shows that AtxE2 hydrolyzes the isopeptide bond between Gly1 and Asp9 selectively. In contrast to the results obtained for astexins-2 and -3, the retention time of astexin-1 did not shift after incubation with AtxE2 and no molecular weight difference was observed in the MS (FIG. S9). This indicates that AtxE2 has specificity toward only the two lasso peptides in its own cluster.

Example 5. AtxE2 does not Hydrolyze Unthreaded Astexin-2

As noted above, we observed unthreaded astexin-2 species in HPLC analyses of extracts of cells harboring pMM37 and pMM40 (FIG. 3). Remarkably, the retention times for these unthreaded species did not change after incubation with AtxE2 (FIG. 5A). To probe this observation further, we purified astexin-2 ΔC3 in its threaded form, and generated an unthreaded form by extensive heat treatment. Both the threaded and unthreaded astexin-2 ΔC3 peptides were treated with 424 nM AtxE2, but only the threaded species exhibited a change in retention time consistent with hydrolysis of the isopeptide bond. Collectively, these results demonstrate that AtxE2 can only function on a knotted structure, likely making it a highly specific enzyme.

Example 6. AtxE1 Hydrolyzes Astexin-1 In Vivo

In contrast to AtxE2, we were unable to solubly express the AtxE1 enzyme. We investigated AtxE1 activity toward astexin-1 in vivo by expressing astexin-1 along with AtxE1 in *E. coli*. Plasmid pMM62 was constructed by introducing the gene for AtxE1 downstream of the astexin-1 biosynthesis cluster in pMM32[4], with its own ribosome binding site. In contrast to the supernatant extracts of pMM32, MALDI results showed both lassoed and linearized versions of astexin-1 in the supernatant of pMM62.

Example 7. Kinetics of Astexin-3 Proteolysis by AtxE2

Figure 7:
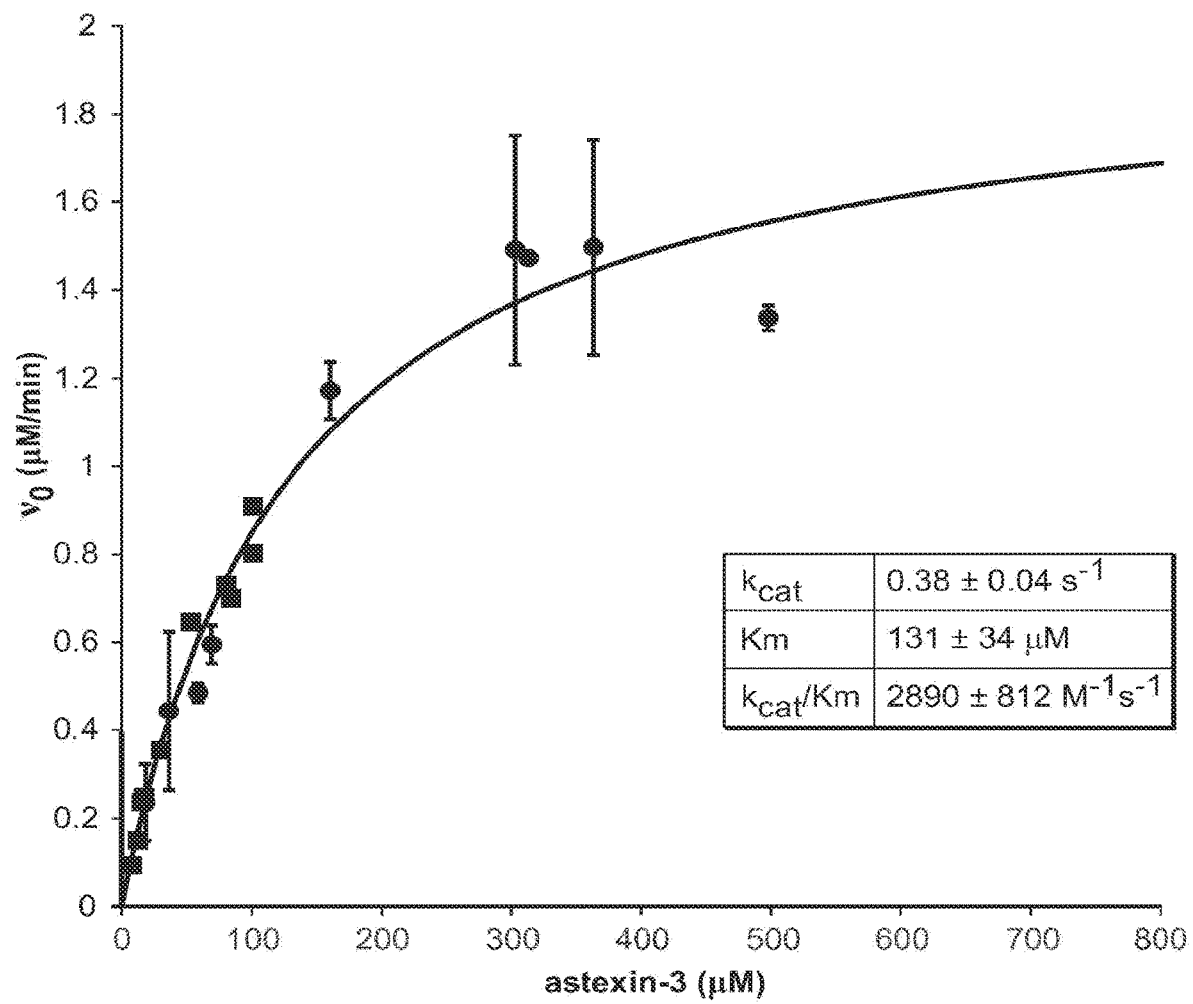
FIG. 7: Michaelis-Menten plot detailing the kinetics of the hydrolysis of astexin-3 by AtxE2. Relevant parameters with 95% confidence intervals are summarized in the inset table. Circles indicate data points obtained in triplicate with the corresponding error bars (standard deviation), while squares represent single measurements. The $R^2$ value for the fit is 0.97.

Tryptophan fluorescence of peptides and proteins has been used extensively to probe changes in their conformation[23]. Astexin-3 contains a single tryptophan positioned right below its ring, which prompted us to look for differences in the emission spectra of the lassoed and linear astexin-3 upon excitation with 275 nm light. The emission intensity at the 340 nm of lassoed astexin-3 is ca. seven fold higher than that of the linearized astexin-3 at the same molar concentration. To calculate $k_{cat}$ and $K_m$ associated with lasso peptide hydrolysis, we carried out protease assays while varying the concentration of astexin-3 at a constant concentration of AtxE2 at 24° C. Measurements were taken using a fluorescence plate reader at discrete time intervals or as final time points from aliquots of reactions quenched after different times. The concentration of AtxE2 (87 nM) was chosen such that astexin-3 would always be in at least 90-fold molar excess relative to the peptidase. We determined the $k_{cat}/K_m$ value for AtxE2 to be $2.9 \times 10^3$ $M^{-1}s^{-1}$, with $k_{cat}$ equal to 0.38 $s^{-1}$ and $K_m$ equal to 131 µM. The data and fit are shown in FIG. 7 along with a summary of the relevant parameters. The $k_{cat}/K_m$ for AtxE2 is several orders of magnitude smaller than that of serine proteases acting on simple peptide substrates ($k_{cat}/K_m \sim 10^7 M^{-1}s^{-1}$)[24]. From homology modeling (see below), AtxE2 most closely resembles prolyl oligopeptidases, and the kinetics of AtxE2 are on par with characterized enzymes in this family[25].

Tryptophan fluorescence of peptides and proteins has been used extensively to probe changes in their conformation[23]. Astexin-3 contains a single tryptophan positioned right below its ring which prompted us to look for differences in the emission spectra of the lassoed and linear astexin-3 upon excitation with 275 nm light. The emission intensity at the 340 nm of lassoed astexin-3 is ca. seven fold higher than that of the linearized astexin-3 at the same molar concentration. To calculate $k_{cat}$ and $K_m$ associated with lasso peptide hydrolysis, we carried out protease assays while varying the concentration of astexin-3 at a constant concentration of AtxE2 at 24° C. Measurements were taken using a fluorescence plate reader at discrete time intervals or as final time points from aliquots of reactions quenched after different times. The concentration of AtxE2 (87 nM) was chosen such that astexin-3 would always be in at least 90-fold molar excess relative to the peptidase.

We determined the $k_{cat}/K_m$ value for AtxE2 to be $2.9 \times 10^3$ $M^{-1}s^{-1}$, with $k_{cat}$ equal to 0.38 $s^{-1}$ and $K_m$ equal to 131 µM. The data and fit are shown in FIG. 7 along with a summary of the relevant parameters. The $k_{cat}/K_m$ for AtxE2 is several orders of magnitude smaller than that of serine proteases acting on simple peptide substrates ($k_{cat}/K_m \sim 10^7 M^{-1}s^{-1}$)[24]. From homology modeling (see below), AtxE2 most closely resembles prolyl oligopeptidases, and the kinetics of AtxE2 are on par with characterized enzymes in this family[25].

Example 8. Serine 527 is the Catalytic Residue in AtxE2

Several serine proteases in the prolyl oligopeptidase family (Pfam 00326) were identified as homologs of AtxE1 and AtxE2 through modeling using the I-TASSER server[26]. The putative catalytic triads are located in the C-terminal regions of both proteins with Ser526-Asp550-His639 being the relevant residues in AtxE1 and Ser527-Glu610-His638 in AtxE2. We wanted to confirm that AtxE2 was catalyzing amide bond hydrolysis using Ser527 as the nucleophile. To this end we expressed and purified the S527A mutant of AtxE2 and assayed its activity toward astexin-3 in vitro. AtxE2 S527A had no activity toward astexin-3, confirming that this serine residue is the catalytic nucleophile.

Example 9. Phylogenetic Analysis of Lasso Peptide Synthetases

With the confirmation that AtxE2 is a bona fide lasso peptide isopeptidase, we revisited our global lasso peptide genome mining data to determine how frequently such isopeptidases are observed in the neighborhood of lasso peptide clusters and whether there are other genes that belong to the clusters. We noted the presence of a GntR homolog and a TonB-dependent transporter (TBDT) in both astexin clusters, and homologs of FecR and FecI in the astexin-1 cluster. The putative clusters in *S. japonicum* and the caulosegnin cluster[4,6] also feature these genes. We used MEME[27] to generate conserved domain motifs for the GntR, isopeptidase, TBDT, FecI and FecR homologs using protein sequences from *A. excentricus, C. segnis* and *S. japonicum* as the training set. As noted above, many previously described lasso peptide gene clusters include an ABC transporter rather than an isopeptidase. Motifs for the lasso peptide ABC transporter were generated from the proteins McjD, CapD and LarE[5,9,11]. Open reading frame translations within 20 kbp of the lasso peptide biosynthesis genes were queried for the presence of these motifs.

Of the 81 clusters that were analyzed, 17 were found to have an isopeptidase, 25 an ABC transporter, and the remaining clusters had neither. Each of the clusters with an isopeptidase also had a TBDT and all except the astexin-2, -3 cluster and *X. gardneri* cluster had homologs of FecR and FecI. A GntR homolog was identified in 13 of the 17 clusters (Table 1). Of the clusters with an ABC transporter, 17 had a B gene homolog that was shorter than a typical B gene by ca. 100 residues, but still carried the essential trasglutaminase catalytic triad located in the C-terminus of these enzymes[10,22,28,29]. In all cases, a second smaller protein annotated as being of unknown function was encoded nearby. It has been noted that the lariatin cluster includes such a protein (termed LarC by the authors)[11]. However, no comparison of the lariatin maturation enzymes to those of other lasso peptides has been done to determine the role of this unknown gene. By looking globally at all the clusters with and without this maturation enzyme, we determined that the shorter protein aligns very well with the N-terminal portions of McjB, CapB, AtxB1, AtxB2, and other "full-length" B gene homologs, and contains a conserved LDXXXXRYFXL motif. This suggests that the function of the B homolog is split between two proteins in these clusters, an observation supported by the fact that LarC is essential for lariatin production[11]. Another novel aspect of our survey of lasso peptide cluster architectures is the identification of putative "B-D" fusion proteins in *Streptococcus suis, Enterococcus faecalis*, and *Ruminococcus albus*. In these organisms, the N-terminal portion of the B homolog is also encoded as a distinct protein, but the C-terminal catalytic domain appears to be fused to the ABC transporter. In one of the *Frankia* CcI3 clusters and the *S. suis* cluster, the C homolog appear to be split between two distinct proteins.

The successful classification of lasso peptide clusters based on architecture alone led us to consider whether sequences of B and C homologs also segregate into distinct clades. To investigate their evolutionary relatedness, we performed a Bayesian phylogenetic analysis on the protein sequences using MrBayes 3.2.1[30-32], a strategy recently used to examine relationships between lanthipeptide clusters[33]. Since there is no structural information on any B and C homologs, we used a secondary structure prediction generated with SPINE-X[34] to assemble an accurate multiple sequence alignment. Thirty putative homologs were discarded from the analysis due to poor alignment. Since the two portions of the "split-B" homologs could experience differing amino acid substitution rates, we chose to use only the C-terminal portion of the proteins for the analysis. Similarly, short regions of the C homolog responsible for ATP binding, $Mg^{2+}$ coordination and two additional conserved domains were chosen as input to MrBayes. All Bayesian MCMC inference analyses were run for at least 5,000,000 generations with 2 sets of 7 chains (1 cold and 6 heated) to convergence as indicated by a value of the average standard deviation of split frequencies below 0.01. A 25% burn-in was accepted before calculating the final statistics.

Figure 8A:
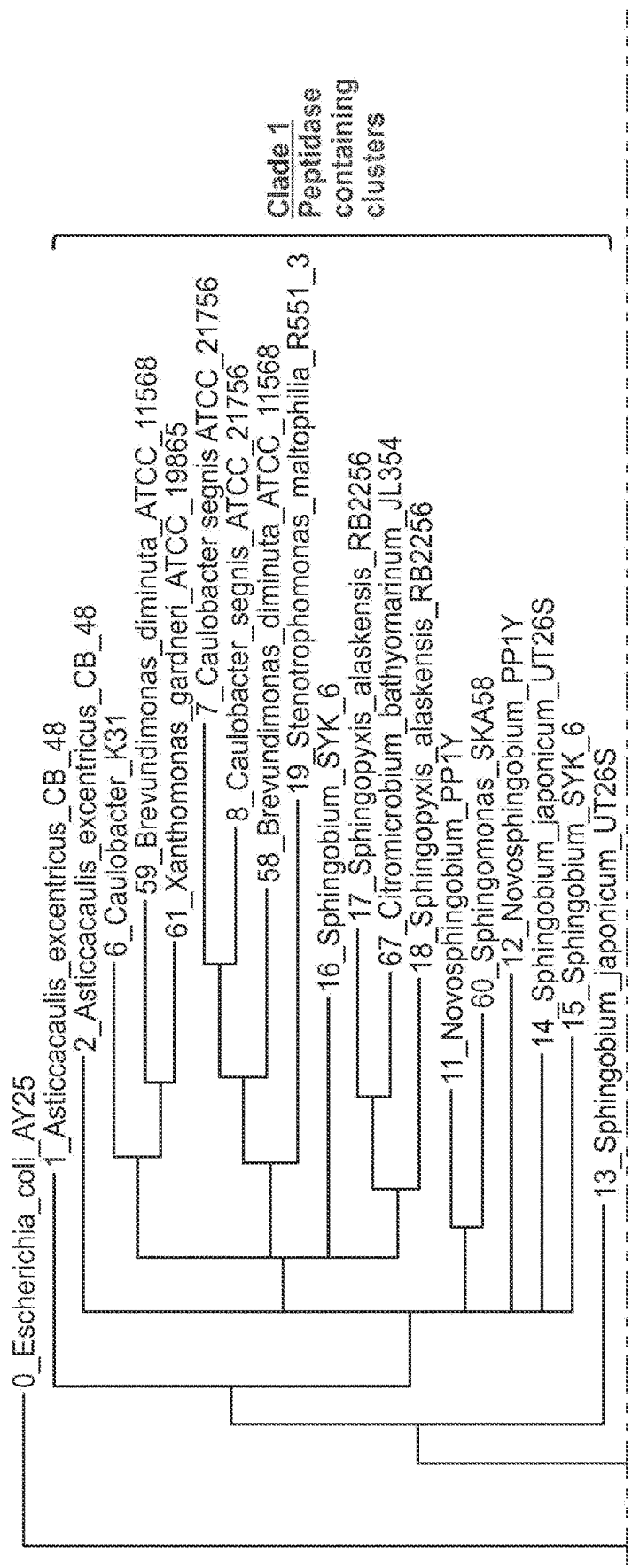
FIG. 8A-B: Phylogenetic tree of known and putative lasso B homologs. A: Clusters containing a peptidase are highlighted in blue, B: Clusters with an ABC transporter are shown in red. Clusters containing only an ABC transporter homolog are presented in black. Thicker line width indicates higher values of the Bayesian posterior probability. Branches with posterior probabilities lower than 0.6 are indicated in the figure.
Figure 8B:
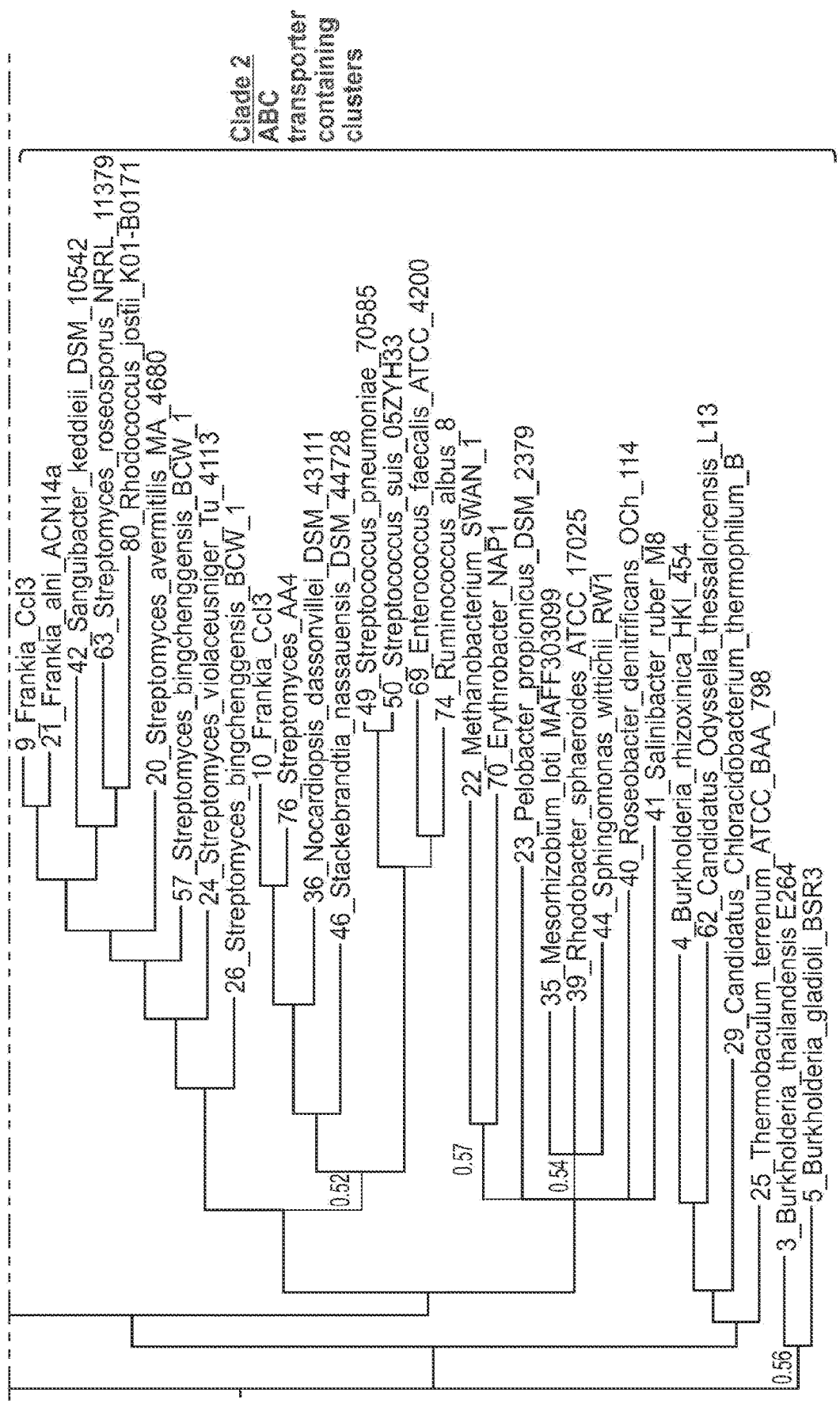

Phylogenetic trees derived from either the B gene homologs or the C gene homologs have similar branching (FIG. 8). These trees segregate into two clear clades. Remarkably, Clade 1 consists almost exclusively of clusters containing an isopeptidase. Clade 2 is made up of canonical lasso peptide clusters with an ABC transporter as well other "biosynthesis-only" clusters with just A, B, and C gene homologs. Even though the genome of *C. bathyomarinum* is incomplete, its membership in Clade 1 suggests that it may be an isopeptidase-containing cluster. Assessing the sequence composition and amino-acid conservation of the precursor peptides provided further support to our two-clade model and allowed the identification of general features of lasso peptide precursors in both clades. Clade 1 core peptides are generally polar, negatively charged, and terminate in an aspartic or glutamic acid residue, while Clade 2 peptides are mostly hydrophobic with patches of positive charge. The conservation of amino acid composition of lasso peptides in the two clades suggested an evolutionary pressure on the function of these natural products.

In this study we describe the first two examples of isopeptidases that act selectively on lasso peptides produced by *A. excentricus*. We demonstrate activity of AtxE2 towards astexin-2 and astexin-3 in vitro and show that AtxE1 can hydrolyze astexin-1 in vivo. In addition to elucidating the kinetic parameters of AtxE2, we used NMR to solve the structure of astexin-3. We establish the identity of astexin-2 as a lasso peptide by mass spectrometry, thus adding to the list of lasso peptides in the astexin family. We present evidence that AtxE1 and AtxE2 catalyze the reverse reaction of lasso peptide synthesis by cleaving the isopeptide bond that was installed during the maturation of the lasso peptides. At least in the case of astexin-2, AtxE2 works by recognizing the lasso topology rather than a specific amino acid sequence since unthreaded astexin-2 is left intact after AtxE2 treatment. This makes AtxE2 stand out in relation to intracellular proteases that target unstructured protein regions for degradation[35]. The discovery that AtxE1 and AtxE2 can deconstruct the astexins also opens up new avenues for engineering these lasso peptides.

Astexins-2 and -3 are intracellular lasso peptides, in contrast to astexin-1, which can be found both in the culture supernatant[4] and in producer cells[13]. Phylogenetic analysis revealed that the astexins belong to the same clade of lasso peptides as the caulosegnins, which is distinct from the clade of capistruin, lariatin and other clusters with an ABC transporter. Furthermore, differences in the gene architectures between the two clades and the sequence composition of their lasso peptides suggest differences in function. MccJ25, capistruin, and lariatin are all antimicrobial peptides. The associated ABC transporter in these Clade 2 peptides serves as exporter and immunity factor, and the sequences of the peptides themselves are evolutionarily attuned to infiltrate susceptible cells by co-opting iron import machinery[36,37] and disabling the RNA polymerase of the target organism[38-40]. Conversely, Clade 1 lasso peptides have a membrane-bound importer protein and a dedicated enzyme to specifically deconstruct the lasso peptide in the cell. Additionally, the expression and degradation of these peptides appears to be tightly controlled by a helix-turn-helix transcriptional repressor and a sigma/anti-sigma pair. This is remarkably similar to biosynthetic and regulatory system of siderophores[41]. In light of this, the natural function of the astexins (and likely other Clade 1 peptides) is more consistent with a type of scavenging molecule that acts through a catch-and-release mechanism.

Another fascinating aspect of the lasso peptide superfamily that remains to be learned is their evolutionary history. For example, did "whole-B" homologs evolve from two genes by fusion, or did the "split-B" architecture emerge through a duplication event followed by selective degradation of redundant domains? Both gene fusion and fission are commonly observed events in prokaryotes with their own set of evolutionary benefits and drawbacks that are highly context dependent[42]. Parsimony suggests that Clade 1 is more ancient simply because the number of evolutionary changes that would have to occur to transform an ABC-transporter cluster into an isopeptidase-type cluster is much greater than the opposite possibility. Regardless of the origins of these clades, the insights that we have gained about the existence of lasso peptide isopeptidases, astexin-2 and -3, and the various architectures of lasso peptide clusters will facilitate engineering and characterization of known and as-yet unknown lasso peptides.

Here we describe the heterologous expression of a lasso peptide gene cluster encoding two lasso peptides, astexin-2 and astexin-3 and solve the solution structure of astexin-3. This cluster also encodes an enzyme annotated as a protease. We show that this enzyme, AtxE2, is a lasso peptide isopeptidase that specifically hydrolyzes astexins-2 and -3 converting them to linear peptides. Astexin-3 is highly thermostable and resists unthreading after extensive heat treatment. In contrast, astexin-2 unthreads upon heat treatment. AtxE2 has no activity toward unthreaded astexin-2 demonstrating that this isopeptidase must recognize a knotted structure in order to function. We also use this isopeptidase as a tool to study evolutionary relationships between lasso peptide gene clusters.

Example 10. AtXE2 Protein and Nucleic Acid Sequences

An AtxE2 polypeptide sequence according to the invention includes the following amino acid sequence:

```
                                          (SEQ ID NO: 1)
MRSSKIRCPGAIRVGTLVTAFGCLPHVAFAAAREAPPVTPEVLVRLADIG

TMSASETTPLLSLSPDGRYVAFQVRQADPVTNLNVFRMVVKATDGATDAI

DVDVGGEYLEWTIPSWGYARNAPSGANLTIQPRWSPSGTHLAYLRQDQGR

VRVWRASVKGEGASPVIEDAYDIEDVQWLDDNTLIYSGRPGFVEAEAEIE

REGRRGWVYDERFHPLTGARPRVLEPISIVYQVLDLKTGTRRAATPTEVA

RLREKPDPLRAMVGRTTFSVSRTDPQNINAPTTLVARRGEGEPVRCDEEA

CQNITRMWGDETANVLYFLRREGWASNEMALYRMPADALKPVRIWHATGL

LQGCERQAKRLICAQESALQPRRLVTLNLTSGQMSPLYDPNPDLSRYRLP

KVERLTLRNRNGIEVFSDLVLPPDYQLGTRLPLVIVQYSSRGFLRGGTGD

ENPILPLATAGFAVLSFHSPRSEASYQRFTSPIAQSKAEYSNWRNRWNIL

HTLEDLIDDLDRRGVIDPARVGLTGLSDGATTVHFGLINSHRFAAAVTSS

CCTDSFTASVMNGPRISGALKAYGIETDQADDGPFWAATSFVVNASRLDT

PLLIQSADEEYLGALPGFTALQQARKPVELITYPNEHHVKWQPAHRLAVY

NRTIDWFREWLMDQSDPAPDKAAQYDRWRALRALRQKSPSPTPAP
```

An AtxE2-encoding nucleic acid sequence is provided below:

```
                                          (SEQ ID NO: 2)
ATGAGGTCGTCTAAGATCCGGTGTCCCGGCGCAATCCGCGTCGGGACCCT

GGTGACGGCGTTTGGCTGCCTCCCGCACGTCGCGTTTGCGGCGGCGCGGG

AGGCGCCCCCGTCACGCCTGAAGTTCTGGTCCGTCTGGCAGACATCGGT

ACGATGAGCGCCAGTGAAACCACACCGCTCCTCAGTCTCTCGCCGGACGG

TCGCTATGTCGCGTTTCAGGTCCGCCAGGCTGACCCTGTGACGAACCTAA

ACGTGTTTCGTATGGTGGTTAAAGCGACGGATGGCGCCACAGATGCCATG

ACGTCGATGTCGGTGGCGAGTATCTGTTCTGGACGATACCCAGTTGGGGG

TATGCCCGAAACGCCCCGTCAGGCGCCAACCTCACCATCCAGCCGCCTG

GTCGCCCTCGGGGACACACCTCGCCTATTTGCGTCAGGACCAGGGGAGGG

TGCGCGTCTGGCGTGCGAGCGTCAAAGGGAGGGGGCCAGTCCTGTCATC

GAAGACGCCTATGATATAGAGGACGTGCAATGGCTGGATGACAACACGCT

GATCTATTCGGGCCGACCGGGTTTCGTCGAGGCTGAGGCCGAAATCGAAC

GCGAGGGACGACGGGGTTGGGTGTATGATGAGCGCTTTCACCCTCTAACC

GGCGCACGCCCGCGTGTGCTGGAGCCGATATCGATCGTTTATCAGGTCTT

GGATCTCAAAACAGGTACGCGCCGGGCGGCGACCCCTACAGAGGTGGCGC
```

```
GCCTCAGAGAAAAGCCAGACCCATTGCGCGCGATGGTGGGGCGGACAACC

TTCAGCGTCAGCCGAACCGACCCTCAAAATATCAACGCGCCAACCACGCT

CGTCGCACGACGTGGGGAGGGAGAACCGGTGCGTTGTGATGAAGAGGCTT

GCCAGAACATTACCCGGATGTGGGGAGATGAGACCGCCAATGTCCTTTAT

TTTCTGCGTCGAGAGGGCTGGGCCAGTAACGAAATGGCCCTTTACCGCAT

GCCCGCTGATGCGCTCAAACCGGTCCGGATTTGGCACGCGACGGGCCTCC

TTCAGGGCTGTGAACGTCAGGCGAAACGTCTCATTTGCGCGCAGGAGTCC

GCCCTTCAGCCCCGCCGTTTGGTGACCCTCAATCTGACCTCAGGTCAAAT

GTCGCCGCTCTATGACCCCAATCCCGACTTGTCGCGCTATCGTCTCCCAA

AGGTCGAGCGTCTGACTCTTCGGAATCGAAACGGCATTGAGGTGTTCAGT

GATCTGGTGCTTCCACCCGACTATCAGCTCGGCACCCGGCTGCCGCTTGT

GATCGTGCAATACAGTTCGCGCGGCTTTCTGCGGGGCGGCACCGGCGATG

AAAATCCGATCCTGCCGCTCGCCACCGCTGGGTTTGCCGTATTGAGCTTC

CATAGTCCTCGCAGCGAAGCCTCGTATCAGAGGTTTACGTCGCCCATAGC

GCAGTCAAAAGCGGAATACAGCAACTGGCGTAATCGCTGGAACATCCTGC

ACACCCTCGAAGATCTGATTGATGATCTGGATCGGAGAGGCGTGATCGAT

CCTGCAAGGGTCGGTCTAACGGGTTTGAGCGATGGGGCCACAACGGTGCA

CTTTGGTCTGATCAATAGCCATCGCTTTGCCGCGGCCGTGACCAGCAGTT

GCTGTACGGACAGCTTCACCGCATCGGTCATGAATGGACCGCGGATCTCA

GGGGCTCTGAAAGCCTACGGCATTGAGACGGATCAGGCCGATGACGGGCC

CTTCTGGGCCGCCACATCGTTTGTCGTGAATGCGAGCCGCCTGGATACGC

CCCTGCTAATCCAGTCCGCAGACGAGGAGTATCTCGGCGCACTTCCCGGC

TTTACCGCCTTGCAGCAAGCCAGAAAGCCTGTTGAGCTCATCATTTACCC

CAACGAGCACCACGTCAAATGGCAGCCGGCGCACCGGCTGGCGGTCTACA

ATCGCACGATAGACTGGTTTCGCTTCTGGCTGATGGATCAGTCAGATCCC

GCACCCGACAAGGCCGCGCAGTACGACCGCTGGCGGGCGTTGCGCGCCCT

CAGGCAGAAATCCCCAAGCCCCACTCCGGCGCCTTAG
```

Example 11. Astexin-2 and Astexin-3 Materials and Methods

Strains and Reagents

XL-1 blue *E. coli* were used for all recombinant DNA steps. Whole genomic DNA (gDNA) was isolated from *A. excentricus* (Strain DSM 4724), purchased from the German Collection of Microorganisms and Cell Cultures (DMSZ), using a standard protocol (Qiagen DNeasy Blood & Tissue Kit). PicoMaxx DNA polymerase was used for PCR amplification with oligonucleotides purchased from IDT. The NheI, XbaI, EcoRI, BamHI, BglII and HindIII restriction enzymes were purchased from New England Biolabs. Synthetic linear peptides were purchased from GenScript and HPLC repurified in house.

Example 12. Constructing Astexin-2 and -3, and atxE2 Expression Vectors

Lasso Peptide Expression Vectors

Primers 1 and 2 (see below) were used to amplify a 3307 base pair product containing the atxA2A3B2C2 cluster from gDNA that included a 118 base pair sequence upstream and a 45 base pair sequence downstream of the gene cluster. The product was digested with NheI and ligated into pQE-80L (Qiagen). The atxA2A3B2C2 cluster was then transferred into pASK-75[14] using primers 3 and 4 and the XbaI and HindIII restriction enzymes to produce plasmid pMM12. Primers 5 and 6 were used to amplify a 3196 base pair product from pMM12 containing the atxA2A3B2C2 gene cluster that included a 23 base pair sequence upstream and a 45 base pair sequence downstream of the gene cluster. The product was digested and ligated in pASK-75 to produce plasmid pMM37. Primers 6 and 7 were used to amplify a 2622 base pair product from pMM12 containing the atxB2C2 genes that included 23 base pairs upstream of the atxB2 gene. The product was digested and ligated in pASK-75 to produce plasmid pMM38. Primers 6 and 8 were used to amplify a 2921 base pair product from pMM12 containing the atxA3B2C2 genes. The product was digested and ligated into pASK-75 to produce plasmid pMM39. Primer pairs 5, 9 and 10, 11 were used to generate two DNA fragments from pMM12, which were overlapped by PCR to generate DNA product 1 that included the atxA2 gene and part of the atxB2 gene. Primer pairs 6, 10 were used to amplify DNA product 2 from pMM12 that included the atxB2 and atxC2 genes. DNA products 1 and 2 were then overlapped by PCR to generate a 2917 bp fragment containing the atxA2B2C2 genes. The product was digested and ligated in pASK-75 to produce plasmid pMM40.

Isopeptidase Expression Vectors

Primers 12 and 13 were used to amplify a 2139 base pair product containing the atxE2 gene from gDNA. The product was digested and ligated into pQE-60 to produce a C-terminally His-tagged AtxE2. The resulting plasmid was called pMM56. To generate a His-tagged S527A mutant of AtxE2, primers 12 and 15 were used to amplify a 1634 base pair fragment from pMM56 that was subsequently overlapped by PCR with a 538 base pair fragment that was amplified from pMM56 using primers 13 and 14. The resulting fragment was digested and ligated into pQE-60 to produce plasmid pMM63. Primers 16 and 17 were used to amplify a 2065 base pair product containing the atxE1 gene from gDNA. The product was digested and ligated into pQE-60 (Qiagen) to make a C-terminally His-tagged AtxE1. This plasmid was called pMM57. Primers 18 and 19 were used to amplify a 2092 base pair fragment from pMM57 containing the sequence of His-tagged AtxE1. The product was digested and ligated into pMM32[4] to produce plasmid pMM62.

Primer Sequences

| Primer 1 | CCCGGCACGTCCGCTAGCTGCTGAACATTCGGGGTA (SEQ ID NO: 9) |
|---|---|
| Primer 2 | CTGGCGGGCGTTGCGCGCTAGCAGGCAGAAATCCCC (SEQ ID NO: 10) |
| Primer 3 | GTGAGAATCCAAAAGCTTAGGCAG (SEQ ID NO: 11) |
| Primer 4 | CTCGCCAATCTAGATGCTGAAC (SEQ ID NO: 12) |
| Primer 5 | GCTTCTAGAACTCAAACCTACAGG (SEQ ID NO: 13) |
| Primer 6 | TCACAGGTCAAGCTTAGGC (SEQ ID NO: 14) |
| Primer 7 | CCATCTAGACAACACACGTGA (SEQ ID NO: 15) |
| Primer 8 | CACTGAGTCTAGAGGCTCACTC (SEQ ID NO: 16) |
| Primer 9 | GCGCCCTGCATCTTAGTCCGCCGACA (SEQ ID NO: 17) |
| Primer 10 | CTAAGATGCAGGGCGCGCGTCACAAC (SEQ ID NO: 18) |
| Primer 11 | GCGCCAGCCCGACGAGC (SEQ ID NO: 19) |
| Primer 12 | GCGTCATCAGCGAATTCCTTGTGAAGGAGAGGTAAGCG (SEQ ID NO: 20) |
| Primer 13 | CTAGCCACCCGGATCCAGGCGCC (SEQ ID NO: 21) |
| Primer 14 | GGTCTAACGGGTTTGGCGGATGGGGCCACAACG (SEQ ID NO: 22) |
| Primer 15 | CGTTGTGGCCCCATCCGCCAAACCCGTTAGACC (SEQ ID NO: 23) |
| Primer 16 | TGCACAGAATTCCCTCAGCAGGAGATTCTAAGCATGC (SEQ ID NO: 24) |
| Primer 17 | CCGCGGACCTAAAAGATCTGGGACATAAGCCC (SEQ ID NO: 25) |
| Primer 18 | TTTCACACAAAGCTTCCTCAGCAGGAG (SEQ ID NO: 26) |
| Primer 19 | GCTCAGCTAATTAAGCTTAGTGATGGTG (SEQ ID NO: 27) |

Heterologous Expression of Astexins-2, -3

E. coli BL21 cells transformed with the pMM37, pMM38, pMM39 or pMM40 plasmids were initially grown in LB medium supplemented with 100 mg/L ampicillin at 37° C. Cells were then subcultured into 500 mL M9 minimal medium (3 g/L Na$_2$HPO$_4$, 1.5 g/L KH$_2$PO$_4$, 0.5 g/L NH$_4$Cl, 0.25 g/L NaCl, 2 g/L glucose, 1 mM $MgSO_4$, and 500 µg/L thiamine, 100 mg/L ampicillin), supplemented with the 20 amino acids (0.04 g/L each) to an $OD_{600}$=0.02. Cultures were induced with 200 µg/L anhydrotetracycline (aTc) upon reaching an $OD_{600}$=0.25 and allowed to grow for 21 hours. Cell pellets were then collected by centrifugation at 12,000×g at 4° C. and washed with 50 mL cold 1× phosphate-buffered saline (PBS) and centrifuged again at the same speed. Washed pellets were resuspended in 20 mL phosphate buffered saline (PBS), boiled for 20 min and centrifuged at 14,000 rpm. Clarified lysates were applied to 500 mg/3 mL Phenomenex Strata C8 SPE columns for extraction into 2.25 mL methanol. Extracts were dried under reduced pressure and reconstituted in 100 µL 50% acetonitrile (ACN) in water solution for HPLC and MALDI analysis.

Testing Bacterial Supernatants for Production of Astexin-2, -3

*E. coli* BL21 cells transformed with the pMM37, pMM38, pMM39 or pMM40 plasmid were initially grown in LB medium supplemented with 100 mg/L ampicillin at 37° C. Cells were then subcultured into 11 mL of 20 amino acid M9 minimal medium to an $OD_{600}$=0.02. Cultures were induced with 200 µg/L aTc upon reaching an $OD_{600}$=0.25 and allowed to grow for 18 hours. Cell-free supernatant was collected by centrifugation at 14,000 rpm and extracted on 100 mg/1 mL Strata C8 SPE columns. Extracts were dried under vacuum and reconstituted in 500 µL 50% ACN. Samples were subsequently diluted 10 fold with 2.5 mg/mL α-Cyano-4-hydroxycinnamic (Sigma) acid matrix solution for MALDI analysis.

Large Scale Purification of Astexin-3 for NMR Spectroscopy and Kinetics Assays

*E. coli* BL21 cells transformed with the pMM39 plasmid were initially grown in LB medium supplemented with 100 mg/L ampicillin at 37° C. Cells were then subcultured into eight 1 liter cultures of 20 amino acid M9 minimal medium to an $OD_{600}$=0.02. Cultures were induced with 200 µg/L aTc upon reaching an $OD_{600}$ of 0.2-0.3 and allowed to grow for 11 hours. Cell pellets were then collected by centrifugation at 12,000×g at 4° C. and washed with 50 mL cold 1×PBS per liter culture. Cells were centrifuged again at the same speed, resuspended in 20 mL 1×PBS per liter culture with 0.25 mg/mL lysozyme (USB), and incubated on ice for 30 min. Cells were subsequently lysed by sonication and centrifuged at 12,000×g. The resulting lysate was boiled for 15 min and centrifuged at 14,000 rpm to remove precipitated proteins. Clarified lysates were applied in two portions to 1 g/6 mL Phenomenex Strata C8 SPE columns for extraction into a total of 16 mL methanol. The extract was dried under reduced pressure, reconstituted in 1 mL 50% ACN/water mixture and injected onto a Zorbax 300SB-C18 Semi-Prep HPLC Column (9.4 by 250 mm, Agilent Technologies) in 14 injections. A solvent gradient was applied to the column at a flow-rate of 4.5 mL/min: 10% ACN for 1 min, ramp up to 50% ACN over 19 min, ramp up to 90% ACN over 5 min, 90% ACN for 5 min, ramp down to 10% ACN in 2 min. Astexin-3 was collected in the 13.7-14.2 min retention time window and lyophilized. The product was then reconstituted in 500 µL 50% ACN/water mixture and HPLC repurified using the same conditions to afford 3.25 mg of >98% pure astexin-3. This product was subsequently dissolved in 200 µL DMSO-d6 for NMR spectroscopy. Astexin-3 was purified in the same fashion for assays with the purified isopeptidase AtxE2. However, the final product was resuspended in PBS.

Expression and Purification of AtxE2 and AtxE2 S527A

*E. coli* BL21 cells transformed with the pMM56 (AtxE2-6his) or pMM63 (AtxE2_S527A-6his) plasmids were grown in LB medium supplemented with 100 mg/L ampicillin at 37° C. Recombinant protein expression was induced with 1 mM isopropyl-β-D-1-thiogalactopyranoside (IPTG) upon reaching an $OD_{600}$=1.0. Protein expression was carried out for 3 hours at 37° C. Cell pellets were then collected by centrifugation at 6,000 rpm at 4° C. for 12 min and resuspended in 40 mL lysis buffer (50 mM $NaH_2PO_4$, 300 mM NaCl, 10 mM imidazole, pH 8). Lysozyme was added to a concentration of 0.25 mg/mL and the cells were incubated for 30 min on ice. Cells were subsequently lysed by sonication and centrifuged at 10,000 rpm for 12 mins at 4° C. Isopeptidase was then purified using Ni-NTA resin (Qiagen) and buffer exchanged into PBS using PD-10 desalting columns (Bio-Rad). Protein purity was greater than 95% as judged by gel electrophoresis and the presence of the histidine-tag was confirmed by Western blotting using anti-His HRP (Sigma) as a probe. Typical yields for AtxE2 and AtxE2 S527A were 300 µg/L culture.

AtxE1 In Vivo Assay

*E. coli* BL21 cells transformed with the pMM32, pMM33[4] or pMM62 plasmid were initially grown in LB medium supplemented with 100 mg/L ampicillin at 37° C. Cells were then subcultured into 11 mL cultures of 20 amino acid M9 minimal medium to an $OD_{600}$=0.02. Cultures were induced with 200 µg/L aTc upon reaching an $OD_{600}$ of 0.2-0.3 and allowed to grow for 48 hours. Cell-free supernatant was collected by centrifugation at 14,000 rpm and extracted on 100 mg/1 mL Strata C8 SPE columns. Extracts were dried under reduced pressure, reconstituted in 200 µL 50% ACN in water and diluted 10 fold with 2.5 mg/mL α-cyano matrix solution for MALDI analysis.

Isopeptidase Assays with Astexin-2, -3 Extracts and Purified Astexin-1

Dried C8 extracts of lysates of cells bearing the pMM39 and pMM40 plasmids were reconstituted in a solution of 20% and 50% ACN in water respectively. Purified and lyophilized astexin-1 was reconstituted in a mixture of 20% ACN in water. 10 µL of the pMM39 extract was added to 40 µL PBS with and without purified AtxE2. 15 µL of pMM40 extract was added to 173 µL PBS with and without purified AtxE2. 15 µL of purified astexin-1 was added to 173 µL PBS with and without purified AtxE2. The final concentration of AtxE2 in all test samples was 860 nM. Reactions were allowed to proceed at RT for 6 hours. Reactions were subsequently quenched at 65° C. for 30 min, cleaned up using Pierce tC18 mini-spin columns and subjected to HPLC and MALDI analysis.

Determination of Kinetic Parameters for Astexin-3

For a typical kinetics run, 100 µL samples of purified astexin-3 at several concentrations were set up in a Costar 96-well black plate (Fisher Scientific) and equilibrated at 24° C. for 30 min. Concentrated AtxE2 was then added to the samples to a final concentration of 87 nM. The reaction was then monitored over a course of 9 hours in a BioTek Synergy 4 plate reader at 24° C. Maximum emission at 340 nm was measured upon excitation with 275 nm light. After the first set of measurements, the reactions were transferred to a thermocycler (Biorad DNA Engine) at 24° C. with a heated lid to minimize evaporation, and three to four additional time points were collected to ensure completion of the reaction. Due to saturation of the fluorescence signal at high initial astexin-3 concentrations, reactions were carried out in thermocycler tubes at 24° C. from the beginning. Portions of the reaction mixture were withdrawn at different time points and quenched by addition of excess volume of cold methanol. Fluorescence of quenched samples was measured at the end of the kinetics run after drying the samples under reduced pressure and reconstituting in 100 μL water. Decrease in fluorescence intensity due to evaporation in the 96-well plate was adjusted for using data from a sample containing no peptidase. The initial rate of reaction ($v_0$) was calculated from the slope of the each individual time course at time zero. Values of $v_0$ from replicates of experiments at the same initial astexin-3 concentration ($S_0$) were averaged. Final $K_m$ and $k_{cat}$ parameters were calculated from a non-linear fit to $v_0$ versus $S_0$ data using MATLAB.

Thermal Stability Assays with Astexins-2, and -3

Extracts of lysates of cells bearing the pMM39 and pMM40 plasmids (prepared as described in Heterologous expression of Astexins-2, -3) were incubated at 95° C. for 3 hours and 98° C. for 2 hours respectively in a heat block (Denville Scientific). Samples were subsequently cooled, dried under reduced pressure and reconstituted in a mixture of 50% ACN in water. Samples were centrifuged at 14,000 rpm for 15 min and any precipitate was discarded prior to HPLC analysis.

Isopeptidase Assay with Unthreaded Astexin-2 ΔC3

Purified astexin-2 ΔC3 (60 μg) was heated at 95° C. for 3 hours in 100 μL 30% ACN water solution using a thermocycler. An identical sample (30 μg) was left unheated as a control. Heat-treated and untreated astexin-2 ΔC3 samples were split into 4 and 2 aliqouts respectively, containing 15 μg peptide each, and dried under reduced pressure. Each of the samples was then resuspended in 60 μL of 1×PBS. Half of the samples were treated with AtxE2 at a final concentration of 424 nM. Reactions were incubated at RT for 6 hours, purified using Pierce tC18 mini-spin columns, dried under reduced pressure, and resuspended in 50 ACN/water mixture for HPLC analysis.

Bioinformatics

As mentioned in the results section, the MEME software suite was used to generate motifs for the GntR, isopeptidase, TonB-dependent transporter (TBDT), FecR, FecI, and ABC transporter homologs. Sequences under the NCBI accession numbers of YP_004088034.1, YP_004088251.1, YP_003593641.1, YP_003546447.1, and BAI99049.1 were used to find 4 motifs for the identification of GntR homologs. Sequences under the NCBI accession numbers of YP_004088038.1, YP_004088246.1, YP_003593635.1, YP_003546450.1, and BAI99045.1 were used to find 6 motifs for the identification of isopeptidase homologs. Sequences under the NCBI accession numbers of YP_004088039.1, YP_004088245.1, YP_003593634.1, YP_003546451.1, and BAI99044.1 were used to find 8 motifs for the identification of TBDT homologs. Sequences under the NCBI accession numbers of YP_004088040.1, YP_003593633.1, YP_003546452.1, and BAI99043.1 were used to find 4 motifs for the identification of FecR homologs. Sequences under the NCBI accession numbers of YP_004088041.1, YP_003593632.1, YP_003546453.1, BAI99042.1 and were used to find 4 motifs for the identification of the FecI homolog. Sequences under the NCBI accession numbers of YP_442961.1, BAL72550.1, and AAD28497.1 were used to find 5 motifs for the identification of the ABC transporter homolog. Scripts implemented in the Perl programming language were used to detect motifs for each homolog in the genome fasta files obtained from the NCBI database. Open reading frames bracketed by a start and a stop codon in all six frames were identified using getorf—a program from the EMBOSS bioinformatics suite[43].

Mass Spectrometry

Acquisition of mass spectra in the m/z 800-4000 range was performed using a 4800 Plus ABSciex MALDI TOF/TOF Analyzer (ABSciex, Framingham, Mass.). Dried samples were reconstituted in a mixture of 50% ACN in water and spun at 14,000 rpm to remove precipitates. Samples were diluted with a 2.5 mg/mL solution of α-cyano matrix prior to spotting onto an Applied Biosystems (ABI) 384 Opti-TOF 123 mm×81 mm SS plate. The instrument was set to positive ion mode for acquiring MS and $MS^2$ (1 kV collision energy) spectra.

NMR Spectra Processing and Model Building

NMR spectra were acquired as described previously[4] with the following changes. 32 averaged scans were collected for 1D experiments with a time domain size of 65,000 points over a spectral window spanning 12 ppm spectral centered at 5.000 ppm. Acquisition times in States-TPPI[44] mode for the gradient selected COSY experiment were 0.341 s in t2 and 0.043 s in t1. Gradient assisted TOCSY experiments were performed with 20, 60 and 120 ms mixing times. 100, 200 and 300 ms mixing times were chosen for the acquisition of the NOESY spectra. Processing of raw data was performed with the MestReNova software package (MestreLab Research, S.S.L., Santiago de Compostella, Spain) with similar parameters as reported previously. Structural modeling under NMR derived constraints was implemented in CYANA 2.1[19] using parameters previously described. Briefly, a linkage statement was added to the CYANA input file to avoid steric violations between atoms in the isopeptide bond. Pseudoatoms were used during the simulated annealing process, but were removed prior to energy minimization with TINKER[20]. A covalent bond between Cγ Asp9 and the HN of Gly1 was specified prior to energy minimization.

References for Example 12

1. Arnison, P. G. et al. Ribosomally synthesized and post-translationally modified peptide natural products: overview and recommendations for a universal nomenclature. *Natural Product Reports* 30, 108-160 (2013).
2. Velasquez, J. E. & van der Donk, W. A. Genome mining for ribosomally synthesized natural products. *Current Opinion in Chemical Biology* 15, 11-21 (2011).
3. Maksimov, M. O., Pan, S. J. & Link, A. J. Lasso peptides: structure, function, biosynthesis, and engineering. *Natural Product Reports* 29, 996-1006 (2012).
4. Maksimov, M. O., Pelczer, I. & Link, A. J. Precursor-centric genome-mining approach for lasso peptide discovery. *Proceedings of the National Academy of Sciences of the United States of America* 109, 15223-15228 (2012).
5. Knappe, T. A. et al. Isolation and structural characterization of capistruin, a lasso peptide predicted from the genome sequence of *Burkholderia thailandensis* E264. *Journal of the American Chemical Society* 130, 11446-11454 (2008).
6. Hegemann, J. D., Zimmermann, M., Xie, X. L. & Marahiel, M. A. Caulosegnins I-III: A Highly Diverse Group of Lasso Peptides Derived from a Single Biosynthetic Gene Cluster. *Journal of the American Chemical Society* 135, 210-222 (2013).
7. Kersten, R. D. et al. A mass spectrometry-guided genome mining approach for natural product peptidogenomics. *Nature Chemical Biology* 7, 794-802 (2011).
8. Solbiati, J. O., Ciaccio, M., Farias, R. N. & Salomon, R. A. Genetic analysis of plasmid determinants for microcin J25 production and immunity. *Journal of Bacteriology* 178, 3661-3663 (1996).

9. Solbiati, J. O. et al. Sequence analysis of the four plasmid genes required to produce the circular peptide antibiotic microcin J25. *Journal of Bacteriology* 181, 2659-2662 (1999).
10. Duquesne, S. et al. Two Enzymes Catalyze the Maturation of a Lasso Peptide in *Escherichia coli*. *Chemistry and Biology* 14, 793-803 (2007).
11. Inokoshi, J., Matsuhama, M., Miyake, M., Ikeda, H. & Tomoda, H. Molecular cloning of the gene cluster for lariatin biosynthesis of *Rhodococcus jostii* K01-B0171. *Applied Microbiology and Biotechnology* 95, 451-60 (2012).
12. Pan, S. J., Rajniak, J., Maksimov, M. O. & Link, A. J. The Role of a Conserved Threonine Residue in the Leader Peptide of Lasso Peptide Precursors. *Chemical Communications* 48, 1880-1882 (2012).
13. Zimmermann, M., Hegemann, Julian D., Xie, X. & Marahiel, Mohamed A. The Astexin-1 Lasso Peptides: Biosynthesis, Stability, and Structural Studies. *Chemistry and Biology* 20, 558-569 (2013).
14. Skerra, A. Use of the Tetracycline Promoter for the Tightly Regulated Production of a Murine Antibody Fragment in *Escherichia-Coli*. *Gene* 151, 131-135 (1994).
15. Wilson, K. A. et al. Structure of microcin J25, a peptide inhibitor of bacterial RNA polymerase, is a lassoed tail. *Journal of the American Chemical Society* 125, 12475-12483 (2003).
16. Loo, J. A., He, J. X. & Cody, W. L. Higher order structure in the gas phase reflects solution structure. *Journal of the American Chemical Society* 120, 4542-4543 (1998).
17. Zirah, S. et al. Topoisomer Differentiation of Molecular Knots by FTICR MS: Lessons from Class II Lasso Peptides. *Journal of the American Society for Mass Spectrometry* 22, 467-479 (2011).
18. Xie, X. L. & Marahiel, M. A. NMR as an Effective Tool for the Structure Determination of Lasso Peptides. *Chembiochem* 13, 621-625 (2012).
19. Guntert, P., Mumenthaler, C. & Wuthrich, K. Torsion angle dynamics for NMR structure calculation with the new program DYANA. *Journal of Molecular Biology* 273, 283-298 (1997).
20. Ponder, J. W. & Richards, F. M. An Efficient Newton-like Method For Molecular Mechanics Energy Minimization Of Large Molecules. *Journal of Computational Chemistry* 8, 1016-1024 (1987).
21. Cornell, W. D. et al. A 2nd Generation Force-field for the Simulation of Proteins, Nucleic Acids, and Organic Molecules. *Journal of the American Chemical Society* 117, 5179-5197 (1995).
22. Yan, K. P. et al. Dissecting the Maturation Steps of the Lasso Peptide Microcin J25 in vitro. *Chembiochem* 13, 1046-1052 (2012).
23. Eftink, M. R. The Use Of Fluorescence Methods To Monitor Unfolding Transitions In Proteins. *Biophysical Journal* 66, 482-501 (1994).
24. Hedstrom, L. Serine protease mechanism and specificity. *Chemical Reviews* 102, 4501-4523 (2002).
25. Nomura, K. Specificity of Prolyl Endopeptidase. *FEBS Letters* 209, 235-237 (1986).
26. Zhang, Y. I-TASSER server for protein 3D structure prediction. *Bmc Bioinformatics* 9(2008).
27. Bailey, T. L. & Elkan, C. Unsupervised Learning of Multiple Motifs in Biopolymers Using Expectation Maximization. *Machine Learning* 21, 51-80 (1995).
28. Pan, S. J., Rajniak, J., Cheung, W. L. & Link, A. J. Construction of a Single Polypeptide that Matures and Exports the Lasso Peptide Microcin J25. *Chembiochem* 13, 367-370 (2012).
29. Severinov, K., Semenova, E., Kazakov, A., Kazakov, T. & Gelfand, M. S. Low-molecular-weight post-translationally modified microcins. *Molecular Microbiology* 65, 1380-1394 (2007).
30. Ronquist, F. & Huelsenbeck, J. P. MrBayes 3: Bayesian phylogenetic inference under mixed models. *Bioinformatics* 19, 1572-1574 (2003).
31. Huelsenbeck, J. P. & Ronquist, F. MRBAYES: Bayesian inference of phylogenetic trees. *Bioinformatics* 17, 754-755 (2001).
32. Altekar, G., Dwarkadas, S., Huelsenbeck, J. P. & Ronquist, F. Parallel metropolis coupled Markov chain Monte Carlo for Bayesian phylogenetic inference. *Bioinformatics* 20, 407-415 (2004).
33. Zhang, Q., Yu, Y., Velasquez, J. E. & van der Donk, W. A. Evolution of lanthipeptide synthetases. *Proceedings of the National Academy of Sciences of the United States of America* 109, 18361-18366 (2012).
34. Faraggi, E., Zhang, T., Yang, Y. D., Kurgan, L. & Zhou, Y. Q. SPINE X: Improving protein secondary structure prediction by multistep learning coupled with prediction of solvent accessible surface area and backbone torsion angles. *Journal of Computational Chemistry* 33, 259-267 (2012).
35. Sauer, R. T. & Baker, T. A. AAA+ Proteases: ATP-Fueled Machines of Protein Destruction. in *Annual Review of Biochemistry*, Vol 80, Vol. 80 (eds. Kornberg, R. D., Raetz, C. R. H., Rothman, J. E. & Thorner, J. W.) 587-612 (2011).
36. Destoumieux-Garzon, D. et al. The iron-siderophore transporter FhuA is the receptor for the antimicrobial peptide microcin J25: role of the microcin Val(11)-Pro (16) beta-hairpin region in the recognition mechanism. *Biochemical Journal* 389, 869-876 (2005).
37. Salomon, R. A. & Farias, R. N. The FhuA Protein Is Involved in Microcin 25 Uptake. *Journal of Bacteriology* 175, 7741-7742 (1993).
38. Adelman, K. et al. Molecular mechanism of transcription inhibition by peptide antibiotic microcin J25. *Molecular Cell* 14, 753-762 (2004).
39. Kuznedelov, K. et al. The Antibacterial Threaded-lasso Peptide Capistruin Inhibits Bacterial RNA Polymerase. *Journal of Molecular Biology* 412, 842-848 (2011).
40. Mukhopadhyay, J., Sineva, E., Knight, J., Levy, R. M. & Ebright, R. H. Antibacterial peptide microcin J25 inhibits transcription by binding within and obstructing the RNA polymerase secondary channel. *Molecular Cell* 14, 739-751 (2004).
41. Noinaj, N., Guillier, M., Barnard, T. J. & Buchanan, S. K. TonB-Dependent Transporters: Regulation, Structure, and Function. in *Annual Review of Microbiology*, Vol 64, 2010, Vol. 64 (eds. Gottesman, S. & Harwood, C. S.) 43-60 (2010).
42. Snel, B., Bork, P. & Huynen, M. Genome evolution—gene fusion versus gene fission. *Trends in Genetics* 16, 9-11 (2000).
43. Rice, P., Longden, I. & Bleasby, A. EMBOSS: The European molecular biology open software suite. *Trends in Genetics* 16, 276-277 (2000).
44. Marion, D., Ikura, M., Tschudin, R. & Bax, A. Rapid recording of 2D NMR spectra without phase cycling.

Application to the study of hydrogen exchange in proteins. *Journal of Magnetic Resonance* 85, 393-399 (1989).

Example 13. Effect of Sequence Alteration on Levels of Astexin-3 Production

The effect of sequence alterations in the Astexin-3 sequence on the level of peptide produced was examined. Variant Astexin-3 peptides were constructed in which the wild-type residue at ring positions 2-8 was replaced with a cysteine residue. The level of production relative to wild-type (WT) is shown.
Wild-type Astexin-3 peptide sequence:

GPTPMVGLDSVSGQYWDQHAPLAD (SEQ ID NO: 7)

| Ring mutant | Sequence | Level of production relative to WT |
|---|---|---|
| P2C mutant: | GCTPMVGLDSVSGQYWDQHAPLAD (SEQ ID NO: 8) | 41% |
| T3C mutant: | GPCPMVGLDSVSGQYWDQHAPLAD (SEQ ID NO: 9) | 58% |
| P4C mutant: | GPTCMVGLDSVSGQYWDQHAPLAD (SEQ ID NO: 10) | 58% |
| M5C mutant: | GPTPCVGLDSVSGQYWDQHAPLAD (SEQ ID NO: 11) | 65% |
| V6C mutant: | GPTPMCGLDSVSGQYWDQHAPLAD (SEQ ID NO: 12) | 62% |
| G7C mutant: | GPTPMVCLDSVSGQYWDQHAPLAD (SEQ ID NO: 13) | trace |
| L8C mutant: | GPTPMVGCDSVSGQYWDQHAPLAD (SEQ ID NO: 14) | 6.5% |

Replacing the naturally occurring amino acid residue at positions 2-6 resulted in astexin-3 levels of 41%-62% of wild-type. In contrast, substitutions at the position 7 resulted in trace amounts of astexin-3, and substitution at position 8 resulted in 6.5% of wild-type. These results suggest that the amino acid at ring positions 6 and 7 is important for astexin-3 expression and/or stability.

Example 14. Characterization of Astexin-1

Materials and Methods

*Asticcacaulis excentricus* CB 48 (Strain DSM 4724) was purchased from the German Collection of Microorganisms and Cell Cultures (DMSZ) and cultivated in the recommended liquid and solid *Caulobacter* medium (2 g/L Bacto peptone, 1 g/L yeast extract and 0.2 g/L $MgSO_4$) without antibiotics at 30° C. XL-1 Blue *E. coli* were used for all recombinant DNA steps and BL21 *E. coli* for lasso peptide production.
Plasmid Construction Whole genomic DNA (gDNA) was isolated from *A. excentricus* using a standard protocol (Qiagen DNeasy Blood & Tissue Kit). PCR amplification was done using PicoMaxx DNA polymerase and oligonucleotides purchased from IDT. The NheI, XbaI and HindIII restriction enzymes were purchased from New England Biolabs. Primers 1 and 2 (see below) were used to amplify a 2746 base pair product containing the atxA1BC cluster from gDNA that included a 106 base pair sequence upstream and a 37 base pair sequence downstream of the atxA1BC gene cluster. The product was digested and ligated in pQE-80L (Qiagen). Primer pairs 3,4 and 5,6 were used to generate two DNA fragments from the resultant plasmid which were overlapped by PCR to generate a product that contained an optimized *E. coli* RBS sequence from pQE-60 (Qiagen) instead of the inverted DNA repeat region between atxA1 and atxB. The resulting fragment was digested and ligated into pASK-75 (1). Primers 7 and 8 were used to amplify a shortened atxA1BC cluster from the resultant plasmid, which contained only 23 base pairs upstream of the atxA1 start codon. This product was ligated into pASK-75 to produce a plasmid named pMM32.
Primer sequences:

| Primer 1 | CCC ACG AAT GGA TAA GGC TAG CAC AGA TTT CTC GTC (SEQ ID NO: 15) |
|---|---|
| Primer 2 | TCG TCC CGT TCG TGA CCG CTA GCC TTC AAT CCC AAA C (SEQ ID NO: 16) |
| Primer 3 | GGT GAG AAT CCA ATC TAG AAC AGA TTT C (SEQ ID NO: 17) |
| Primer 4 | AAT TTC TCC TCT TTA ATT CAG TCC TGG TTG ATG C (SEQ ID NO: 18) |
| Primer 5 | TAA AGA GGA GAA ATT AAA TGT ACG AAT TAA ACG ACG G (SEQ ID NO: 19) |
| Primer 6 | TCG CCA AAA GCT TCT TCA ATC (SEQ ID NO: 20) |
| Primer 7 | CAT GAA TGT CTA GAG CTA AAT GAA AG (SEQ ID NO: 21) |
| Primer 8 | CTT CAC AGG TCA AGC TTC TTC AAT C (SEQ ID NO: 22) |

Heterologous Expression of Astexin-1

*E. coli* BL21 cells transformed with pMM32 were initially grown in LB medium supplemented with 100 mg/L ampicillin at 37° C. Cells were then subcultured into 2×M9 minimal medium (6 g/L $Na_2HPO_4$, 3 g/L $KH_2PO_4$, 1 g/L $NH_4Cl$, 0.5 g/L NaCl, 3 mg/L $CaCl_2$, 2 g/L glucose, 1 mM $MgSO_4$, and 500 µg/L thiamine, 100 mg/L ampicillin), supplemented with the 20 amino acids (0.04 g/L each) to the desired $OD_{600}$. Cultures were induced with 200 µg/L anhydrotetracycline (aTc) upon reaching an appropriate $OD_{600}$ and allowed to grow for an indicated time period (see below).

Induction Time Experiment

An overnight culture of pMM32 bearing cells was sub-cultures into 100 mL M9 minimal medium to an initial $OD_{600}$ of 0.02. Individual 6 mL samples of culture were withdrawn at $OD_{600}$ of 0.09, 0.14, 0.23, 0.34, 0.43, 0.54, 0.67, 0.81, 1.18 and induced with aTc at that time. A sample of culture that had not been induced was also saved for analysis. After 48 hours of expression, each of the culture samples was spun down at 8,000×g, and 5 mL of the cell-free supernatant was applied to 100 mg/1 mL Strata C8 SPE columns. The columns were eluted with 0.75 mL methanol and subsequently dried under reduced pressure. Each extract sample was resuspended in 200 µL 50% ACN/water mixture, diluted 10-fold and analyzed by MALDI-TOF mass spectrometry. Areas under the curve for astexin-1 and truncated variants were calculated using Data Explorer (Applied Biosystems).

Extraction and Purification of Astexin-1

Determining Retention Time:

20 mL of cell-free supernatant from a pMM32 culture induced at $OD_{600}$ of 0.23 was applied to a 1 mL Phenomenex Strata C8 SPE column containing 100 mg of packing. The column was washed with two column volumes (2 mL) of water and eluted in a stepwise fashion by adding 0.75 mL of 3%, 5%, 7%, 9%, 11%, 13%, 15%, and 17% acetonitrile (ACN) in water. All elutions were dried under reduced pressure and reconstituted in 100 µL 50% ACN in water solution, diluted 10-fold and analyzed by MALDI-TOF mass spectrometry for the presence of astexin-1. The 9% to 17% fractions were combined and injected onto a Zorbax 300SB-C18 Semi-Prep HPLC Column (9.4 by 250 mm, Agilent Technologies) in 3 injections. A solvent gradient was applied to the column at a flow-rate of 4.5 mL/min: 10% A for 1 min, ramp up to 50% A over 19 min, ramp up to 90% A over 5 min, 90% A for 5 min, ramp down to 10% A in 2 min where A is acetonitrile/0.1% TFA and the balance is water with 0.1% TFA. Fractions were collected at four retention time windows: 8-12 min, 15-18.7 min, 11.9-15.1 min, and 18.6-21.2 min. Each fraction was tested by MALDI-TOF mass spectrometry for the presence of astexin-1. The 11.9-15.1 min fraction had the most astexin-1 signal and contained a prominent cluster of peaks between 11.4 and 13.2 min. A fresh extract was made from 20 mL of cell-free supernatant in the same fashion and the 13.1 min peak was purified from and confirmed to be the peptide of interest by MALDI-TOF mass spectrometry.

Large Scale:

Three liters of cell-free supernatant from 3 1 L pMM32 cultures induced between $OD_{600}$ of 0.21 and 0.26 were split into 14 214 mL aliquots. Using a peristaltic pump, the aliquots were sequentially applied to 4 Phenomenex Strata C8 SPE columns (1 g packing/6 mL volume). After applying a single aliquot, the columns were washed with two column volumes (12 mL) of water and eluted in a stepwise fashion by adding 5 mL of 1%, 3%, 5% acetonitrile (ACN) in water, followed by 17% ACN in water and 11 mL methanol. The 17% ACN in water elution was saved each time. This was repeated for all aliquots of culture supernatant, to afford a final eluent volume of 140 mL that was subsequently dried under reduced pressure. 50% ACN in water (2 mL) was used to reconstitute the extract which was then centrifuged at 14,000 rpm for 30 min to remove insoluble material. The clarified product was lyophilized and reconstituted in 600 µl 50% ACN in water. The previously determined retention time of 13.1 min on the HPLC gradient was used to purify crude astexin-1 using a shortened version of the gradient described above: 10% A for 1 min, ramp up to 38% A over 13.3 min, ramp up to 90% A over 5 min, 90% A for 5 min, ramp down to 10% A in 2 min. The eluent from the HPLC was lyophilized, reconstituted by adding 300 µL 50% ACN in water and re-purified on the HPLC to yield 780 µg of product by $A_{280}$ absorbance. The eluent from the HPLC was again lyophilized, reconstituted by adding 200 µL 50% ACN in water and purified on the HPLC to yield 585 µg of product. The eluent from the HPLC was lyophilized and reconstituted by adding 200 µL 50% ACN and purified for a third time to afford the final product.

NMR Spectra Processing and Model Building

One-dimensional spectra were processed using 0.3 Hz exponential apodization, one time zero filling, manual phase correction and segmental baseline correction. 2D COSY spectra were presented in magnitude mode after zero filling in both dimensions and using sine bell or sine square apodization in combination with additional Gaussian broadening of 5-10 Hz. Typical 2D NOESY data processing parameters included zero filling in each dimension to a final size of 1024×4096 data matrix in the frequency domain, apodization with cosine square or cosine function in combination of Gaussian broadening of 5-10 Hz, interactive phase correction and baseline correction using the Whittaker smoother function in MestReNova (MNova). Volume integrals of the crosspeaks were taken by the function provided in MNova.

Simulated annealing was performed using CYANA 2.1 (2). Correct handling of pseudoatom restraints was done internally through the software package. A set of 200 randomly structures were annealed under NMR constraints. A linkage statement was added to the CYANA sequence file to eliminate steric repulsion between the N of Gly1 and the Cγ of Asp9 without directly enforcing the linkage. All pseudoatoms, two N-terminal hydrogens, and a $C_\delta$ oxygen or Asp9 were removed from all models in the PDB file. Twenty structures with the least restraint violations were then subjected to energy minimization using TINKER (3) in the absence of NMR derived constraints and using the amber94 (4) force field model. The Asp9 Cγ to HN Gly1 isopeptide bond was specified in the TINKER input file to enforce the linkage during energy minimization. Structure analysis was done with Visual Molecular Dynamics (VIVID) (5). Electrostatic potential maps were generate using the Adaptive Poisson-Boltzmann Solver (6-10) and PDB2PQR (11-14). PROCHECK-NMR was used to validate the structure ensemble and generate a Ramachandran plot (15).

References for Example 14

1. Skerra A (1994) Use of the Tetracycline Promoter for the Tightly Regulated Production of a Murine Antibody Fragment in *Escherichia-Coli*. *Gene* 151(1-2):131-135.
2. Guntert P, Mumenthaler C, & Wuthrich K (1997) Torsion angle dynamics for NMR structure calculation with the new program DYANA. *J. Mol. Biol.* 273(1):283-298.
3. Ponder J W & Richards F M (1987) An efficient newton-like method for molecular mechanics energy minimization of large molecules. *Journal of Computational Chemistry* 8(7):1016-1024.
4. Cornell W D, et al. (1996) A second generation force field for the simulation of proteins, nucleic acids, and organic molecules (vol 117, pg 5179, 1995). *J Am. Chem. Soc.* 118(9):2309-2309.
5. Humphrey W, Dalke A, & Schulten K (1996) VMD: Visual molecular dynamics. *Journal of Molecular Graphics* 14(1):33-38.
6. Baker N A, Sept D, Joseph S, Holst M J, & McCammon J A (2001) Electrostatics of nanosystems: Application to microtubules and the ribosome. *Proceedings of the National Academy of Sciences* 98(18):10037-10041.
7. Bank R E & Holst M (2003) A New Paradigm for Parallel Adaptive Meshing Algorithms. *SIAM Review* 45(2):291-323.
8. Holst M (2001) Adaptive Numerical Treatment of Elliptic Systems on Manifolds. *Advances in Computational Mathematics* 15(1):139-191.
9. Holst M & Saied F (1993) Multigrid solution of the Poisson-Boltzmann equation. *Journal of Computational Chemistry* 14(1):105-113.
10. Holst M J & Saied F (1995) Numerical solution of the nonlinear Poisson-Boltzmann equation: Developing more robust and efficient methods. *Journal of Computational Chemistry* 16(3):337-364.
11. Dolinsky T J, et al. (2007) PDB2PQR: expanding and upgrading automated preparation of biomolecular structures for molecular simulations. *Nucleic Acids Res* 35(suppl 2):W522-W525.
12. Dolinsky T J, Nielsen J E, McCammon J A, & Baker N A (2004) PDB2PQR: an automated pipeline for the setup of Poisson-Boltzmann electrostatics calculations. *Nucleic Acids Res* 32(suppl 2):W665-W667.
13. Li H, Robertson A D, & Jensen J H (2005) Very fast empirical prediction and rationalization of protein pKa values. *Proteins: Structure, Function, and Bioinformatics* 61(4):704-721.
14. Czodrowski P, Dramburg I, Sotriffer C A, & Klebe G (2006) Development, validation, and application of adapted PEOE charges to estimate pKa values of functional groups in protein-ligand complexes. *Proteins: Structure, Function, and Bioinformatics* 65(2):424-437.
15. Laskowski R A, Macarthur M W, Moss D S, & Thornton J M (1993) Procheck—a Program to Check the Stereochemical Quality of Protein Structures. *J Appl Crystallogr* 26:283-291.

The foregoing description is intended to illustrate and not to limit the scope of the invention, which is defined by the scope of the appended claims. Other embodiments are within the scope of the following claims.

What is claimed is:

1. A substantially purified Astexin-3 peptide comprising the amino acid sequence GPTPMVGLDSVSGQY-WDQHAPLAD (SEQ ID NO:7); wherein the glycine residue (G) at position 1 is covalently bound to the aspartic acid residue (D) at position 9, thereby generating a lassoed peptide.

2. The peptide of claim 1, wherein the peptide is less than 50 amino acids.

3. The peptide of claim 1, wherein the peptide is less than 35 amino acids.

4. A non-naturally occurring polynucleotide sequence encoding the peptide of claim 1, wherein the non-naturally occurring polynucleotide sequence includes at least one codon that differs from a naturally occurring polynucleotide sequence.

5. The non-naturally occurring polynucleotide sequence according to claim 4, wherein the non-naturally occurring polynucleotide sequence includes a cis acting regulatory element.

6. The non-naturally occurring polynucleotide sequence according to claim 4, further comprising a selectable marker, an origin of replication, or both.

7. An Astexin-3 fusion protein comprising the amino acid sequence GPTPMVGLDSVSGQYWDQHAPLAD (SEQ ID NO:7) and a second protein moiety, wherein the N-terminus of the second protein moiety is linked via a peptide bond to the C-terminus of SEQ ID NO:7.

8. The Astexin-3 fusion protein of claim 7, wherein the glycine residue (G) at position 1 of SEQ ID NO:7 is covalently bound to the aspartic acid residue (D) at position 9 of SEQ ID NO:7, thereby generating a lassoed fusion protein.

9. A non-naturally occurring polynucleotide sequence encoding the peptide of claim 7.

10. A substantially purified Astexin-2 peptide comprising the amino acid sequence GLTQIQALDDSVSGQF-RDQLGLSAD (SEQ ID NO:5) wherein the glycine residue (G) at position 1 is covalently bound to the aspartic acid residue (D) at position 9, thereby generating a lassoed peptide.

11. The peptide of claim 10, wherein the peptide is less than 50 amino acids.

12. The peptide of claim 10, wherein the peptide is less than 35 amino acids.

13. A non-naturally occurring polynucleotide sequence encoding the peptide of claim 10, wherein the non-naturally occurring polynucleotide sequence includes at least one codon that differs from a naturally occurring polynucleotide sequence.

14. The non-naturally occurring polynucleotide sequence according to claim 13, wherein the non-naturally occurring polynucleotide sequence includes a cis acting regulatory element.

15. The non-naturally occurring polynucleotide sequence according to claim 13, further comprising a selectable marker, an origin of replication, or both.

16. An Astexin-2 fusion protein comprising the amino acid sequence GLTQIQALDDSVSGQFRDQLGLSAD (SEQ ID NO:5) and a second protein moiety, wherein the N-terminus of the second protein moiety is linked via a peptide bond to the C-terminus of SEQ ID NO:5.

17. The Astexin-2 fusion protein of claim 16, wherein the glycine residue (G) at position 1 of SEQ ID NO:5 is covalently bound to the aspartic acid residue (D) at position 9 of SEQ ID NO:5, thereby generating a lassoed fusion protein.

18. A non-naturally occurring polynucleotide sequence encoding the peptide of claim 16.

\* \* \* \* \*

SEQUENCE LISTING

<160> NUMBER OF SEQ ID NOS: 48

<210> SEQ ID NO 1
<211> LENGTH: 695
<212> TYPE: PRT
<213> ORGANISM: Asticcacaulis excentricus

<400> SEQUENCE: 1

Met Arg Ser Ser Lys Ile Arg Cys Pro Gly Ala Ile Arg Val Gly Thr
1               5                   10                  15

Leu Val Thr Ala Phe Gly Cys Leu Pro His Val Ala Phe Ala Ala Ala
            20                  25                  30

Arg Glu Ala Pro Pro Val Thr Pro Glu Val Leu Val Arg Leu Ala Asp
        35                  40                  45

Ile Gly Thr Met Ser Ala Ser Glu Thr Thr Pro Leu Leu Ser Leu Ser
    50                  55                  60

Pro Asp Gly Arg Tyr Val Ala Phe Gln Val Arg Gln Ala Asp Pro Val
65                  70                  75                  80

Thr Asn Leu Asn Val Phe Arg Met Val Val Lys Ala Thr Asp Gly Ala
                85                  90                  95

Thr Asp Ala Ile Asp Val Asp Val Gly Gly Glu Tyr Leu Phe Trp Thr
            100                 105                 110

Ile Pro Ser Trp Gly Tyr Ala Arg Asn Ala Pro Ser Gly Ala Asn Leu
        115                 120                 125

Thr Ile Gln Pro Arg Trp Ser Pro Ser Gly Thr His Leu Ala Tyr Leu
    130                 135                 140

Arg Gln Asp Gln Gly Arg Val Arg Val Trp Arg Ala Ser Val Lys Gly
145                 150                 155                 160

Glu Gly Ala Ser Pro Val Ile Glu Asp Ala Tyr Asp Ile Glu Asp Val
                165                 170                 175

Gln Trp Leu Asp Asp Asn Thr Leu Ile Tyr Ser Gly Arg Pro Gly Phe
            180                 185                 190

Val Glu Ala Glu Ala Glu Ile Glu Arg Glu Gly Arg Arg Gly Trp Val
        195                 200                 205

Tyr Asp Glu Arg Phe His Pro Leu Thr Gly Ala Arg Pro Arg Val Leu
    210                 215                 220

Glu Pro Ile Ser Ile Val Tyr Gln Val Leu Asp Leu Lys Thr Gly Thr

```
            225                 230                 235                 240
Arg Arg Ala Ala Thr Pro Thr Glu Val Ala Arg Leu Arg Glu Lys Pro
                245                 250                 255

Asp Pro Leu Arg Ala Met Val Gly Arg Thr Thr Phe Ser Val Ser Arg
                260                 265                 270

Thr Asp Pro Gln Asn Ile Asn Ala Pro Thr Thr Leu Val Ala Arg Arg
                275                 280                 285

Gly Glu Gly Glu Pro Val Arg Cys Asp Glu Glu Ala Cys Gln Asn Ile
            290                 295                 300

Thr Arg Met Trp Gly Asp Glu Thr Ala Asn Val Leu Tyr Phe Leu Arg
305                 310                 315                 320

Arg Glu Gly Trp Ala Ser Asn Glu Met Ala Leu Tyr Arg Met Pro Ala
                325                 330                 335

Asp Ala Leu Lys Pro Val Arg Ile Trp His Ala Thr Gly Leu Leu Gln
                340                 345                 350

Gly Cys Glu Arg Gln Ala Lys Arg Leu Ile Cys Ala Gln Glu Ser Ala
            355                 360                 365

Leu Gln Pro Arg Arg Leu Val Thr Leu Asn Leu Thr Ser Gly Gln Met
        370                 375                 380

Ser Pro Leu Tyr Asp Pro Asn Pro Asp Leu Ser Arg Tyr Arg Leu Pro
385                 390                 395                 400

Lys Val Glu Arg Leu Thr Leu Arg Asn Arg Asn Gly Ile Glu Val Phe
                405                 410                 415

Ser Asp Leu Val Leu Pro Pro Asp Tyr Gln Leu Gly Thr Arg Leu Pro
                420                 425                 430

Leu Val Ile Val Gln Tyr Ser Ser Arg Gly Phe Leu Arg Gly Gly Thr
            435                 440                 445

Gly Asp Glu Asn Pro Ile Leu Pro Leu Ala Thr Ala Gly Phe Ala Val
            450                 455                 460

Leu Ser Phe His Ser Pro Arg Ser Glu Ala Ser Tyr Gln Arg Phe Thr
465                 470                 475                 480

Ser Pro Ile Ala Gln Ser Lys Ala Glu Tyr Ser Asn Trp Arg Asn Arg
                485                 490                 495

Trp Asn Ile Leu His Thr Leu Glu Asp Leu Ile Asp Asp Leu Asp Arg
                500                 505                 510

Arg Gly Val Ile Asp Pro Ala Arg Val Gly Leu Thr Gly Leu Ser Asp
            515                 520                 525

Gly Ala Thr Thr Val His Phe Gly Leu Ile Asn Ser His Arg Phe Ala
            530                 535                 540

Ala Ala Val Thr Ser Ser Cys Cys Thr Asp Ser Phe Thr Ala Ser Val
545                 550                 555                 560

Met Asn Gly Pro Arg Ile Ser Gly Ala Leu Lys Ala Tyr Gly Ile Glu
                565                 570                 575

Thr Asp Gln Ala Asp Asp Gly Pro Phe Trp Ala Ala Thr Ser Phe Val
                580                 585                 590

Val Asn Ala Ser Arg Leu Asp Thr Pro Leu Leu Ile Gln Ser Ala Asp
            595                 600                 605

Glu Glu Tyr Leu Gly Ala Leu Pro Gly Phe Thr Ala Leu Gln Gln Ala
        610                 615                 620

Arg Lys Pro Val Glu Leu Ile Ile Tyr Pro Asn Glu His Val Lys
625                 630                 635                 640

Trp Gln Pro Ala His Arg Leu Ala Val Tyr Asn Arg Thr Ile Asp Trp
                645                 650                 655
```

Phe Arg Phe Trp Leu Met Asp Gln Ser Asp Pro Ala Pro Asp Lys Ala
        660                 665                 670

Ala Gln Tyr Asp Arg Trp Arg Ala Leu Arg Ala Leu Arg Gln Lys Ser
    675                 680                 685

Pro Ser Pro Thr Pro Ala Pro
    690                 695

<210> SEQ ID NO 2
<211> LENGTH: 2088
<212> TYPE: DNA
<213> ORGANISM: Asticcacaulis excentricus

<400> SEQUENCE: 2

| | | | | | |
|---|---|---|---|---|---|
| atgaggtcgt | ctaagatccg | gtgtcccggc | gcaatccgcg | tcgggaccct | ggtgacggcg | 60 |
| tttggctgcc | tcccgcacgt | cgcgtttgcg | gcggcgcggg | aggcgccccc | cgtcacgcct | 120 |
| gaagttctgg | tccgtctggc | agacatcggt | acgatgagcg | ccagtgaaac | cacaccgctc | 180 |
| ctcagtctct | cgccggacgg | tcgctatgtc | gcgtttcagg | tccgccaggc | tgaccctgtg | 240 |
| acgaacctaa | acgtgtttcg | tatggtggtt | aaagcgacgg | atggcgccac | agatgccatc | 300 |
| gacgtcgatg | tcggtggcga | gtatctgttc | tggacgatac | ccagttgggg | gtatgcccga | 360 |
| aacgccccgt | caggcgccaa | cctcaccatc | cagccgcgct | ggtcgcccctc | ggggacacac | 420 |
| ctcgcctatt | tgcgtcagga | ccaggggagg | gtgcgcgtct | ggcgtgcgag | cgtcaaaggg | 480 |
| gagggggcca | gtcctgtcat | cgaagacgcc | tatgatatag | aggacgtgca | atggctggat | 540 |
| gacaacacgc | tgatctattc | gggccgaccg | ggtttcgtcg | aggctgaggc | cgaaatcgaa | 600 |
| cgcgagggac | gacggggttg | ggtgtatgat | gagcgctttc | accctctaac | cggcgcacgc | 660 |
| ccgcgtgtgc | tggagccgat | atcgatcgtt | tatcaggtct | tggatctcaa | aacaggtacg | 720 |
| cgccgggcgg | cgacccctac | agaggtggcg | cgcctcagag | aaaagccaga | cccattgcgc | 780 |
| gcgatggtgg | ggcggacaac | cttcagcgtc | agccgaaccg | accctcaaaa | tatcaacgcg | 840 |
| ccaaccacgc | tcgtcgcacg | acgtggggag | ggagaaccgg | tgcgttgtga | tgaagaggct | 900 |
| tgccagaaca | ttacccggat | gtggggagat | gagaccgcca | atgtcctta | ttttctgcgt | 960 |
| cgagagggct | gggccagtaa | cgaaatggcc | ctttaccgca | tgcccgctga | tgcgctcaaa | 1020 |
| ccggtccgga | tttggcacgc | gacgggcctc | cttcagggct | gtgaacgtca | ggcgaaacgt | 1080 |
| ctcatttgcg | cgcaggagtc | cgcccttcag | ccccgccgtt | tggtgaccct | caatctgacc | 1140 |
| tcaggtcaaa | tgtcgccgct | ctatgacccc | aatcccgact | tgtcgcgcta | tcgtctccca | 1200 |
| aaggtcgagc | gtctgactct | tcggaatcga | aacggcattg | aggtgttcag | tgatctggtg | 1260 |
| cttccacccg | actatcagct | cggcaccccgg | ctgccgcttg | tgatcgtgca | atacagttcg | 1320 |
| cgcggctttc | tgcggggcgg | caccggcgat | gaaaatccga | tcctgccgct | cgccaccgct | 1380 |
| gggtttgccg | tattgagctt | ccatagtcct | cgcagcgaag | cctcgtatca | gaggtttacg | 1440 |
| tcgcccatag | cgcagtcaaa | agcggaatac | agcaactggc | gtaatcgctg | gaacatcctg | 1500 |
| cacaccctcg | aagatctgat | tgatgatctg | gatcggagag | gcgtgatcga | tcctgcaagg | 1560 |
| gtcggtctaa | cgggtttgag | cgatgggggcc | acaacggtgc | actttggtct | gatcaatagc | 1620 |
| catcgctttg | ccgcggccgt | gaccagcagt | tgctgtacgg | acagcttcac | cgcatcggtc | 1680 |
| atgaatggac | cgcggatctc | agggggctctg | aaagcctacg | gcattgagac | ggatcaggcc | 1740 |
| gatgacgggc | ccttctgggc | cgccacatcg | tttgtcgtga | atgcgagccg | cctggatacg | 1800 |
| ccccctgctaa | tccagtccgc | agacgaggag | tatctcggcg | cacttcccgg | ctttaccgcc | 1860 |

-continued

```
ttgcagcaag ccagaaagcc tgttgagctc atcatttacc ccaacgagca ccacgtcaaa    1920
tggcagccgg cgcaccggct ggcggtctac aatcgcacga tagactggtt tcgcttctgg    1980
ctgatggatc agtcagatcc cgcacccgac aaggccgcgc agtacgaccg ctggcgggcg    2040
ttgcgcgccc tcaggcagaa atccccaagc cccactccgg cgccttag                 2088
```

```
<210> SEQ ID NO 3
<211> LENGTH: 23
<212> TYPE: PRT
<213> ORGANISM: Asticcacaulis excentricus
<220> FEATURE:
<223> OTHER INFORMATION: Contains a residue 1 to 9 covalent bond

<400> SEQUENCE: 3

Gly Leu Ser Gln Gly Val Glu Pro Asp Ile Gly Gln Thr Tyr Phe Glu
1               5                   10                  15

Glu Ser Arg Ile Asn Gln Asp
            20

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met His Thr Pro Ile Ile Ser Thr Thr Val Gln Pro Lys Thr
1               5                   10

<210> SEQ ID NO 5
<211> LENGTH: 25
<212> TYPE: PRT
<213> ORGANISM: Asticcacaulis excentricus

<400> SEQUENCE: 5

Gly Leu Thr Gln Ile Gln Ala Leu Asp Asp Ser Val Ser Gly Gln Phe
1               5                   10                  15

Arg Asp Gln Leu Gly Leu Ser Ala Asp
            20                  25

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Lys Arg Thr Thr Ile Ala Ala Arg Arg Val Gly Leu Ile Asp Leu
1               5                   10                  15

Gly Lys Ala Thr Arg Gln Thr Lys
            20

<210> SEQ ID NO 7
<211> LENGTH: 24
<212> TYPE: PRT
<213> ORGANISM: Asticcacaulis excentricus

<400> SEQUENCE: 7

Gly Pro Thr Pro Met Val Gly Leu Asp Ser Val Ser Gly Gln Tyr Trp
```

```
Asp Gln His Ala Pro Leu Ala Asp
            20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Arg Thr Tyr Asn Arg Ser Leu Pro Ala Arg Ala Gly Leu Thr Asp
1               5                   10                  15

Leu Gly Lys Val Thr Thr His Thr Lys
            20                  25

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccggcacgt ccgctagctg ctgaacattc ggggta                           36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggcgggcg ttgcgcgcta gcaggcagaa atcccc                           36

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgagaatcc aaaagcttag gcag                                        24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcgccaatc tagatgctga ac                                          22

<210> SEQ ID NO 13
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
gcttctagaa ctcaaaccta cagg                                          24

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcacaggtca agcttaggc                                                19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccatctagac aacacacgtg a                                             21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cactgagtct agaggctcac tc                                            22

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcgccctgca tcttagtccg ccgaca                                        26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctaagatgca gggcgcgcgt cacaac                                        26

<210> SEQ ID NO 19
<211> LENGTH: 17
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 19
gcgccagccc gacgagc                                                    17

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcgtcatcag cgaattcctt gtgaaggaga ggtaagcg                              38

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctagccaccc ggatccaggc gcc                                             23

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtctaacgg gtttggcgga tggggccaca acg                                  33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgttgtggcc ccatccgcca aacccgttag acc                                  33

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcacagaat tccctcagca ggagattcta agcatgc                              37

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ccgcggacct aaaagatctg ggacataagc cc                           32

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tttcacacaa agcttcctca gcaggag                                 27

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctcagctaa ttaagcttag tgatggtg                                28

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 28

Leu Asp Xaa Xaa Xaa Xaa Arg Tyr Phe Xaa Leu
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
1               5

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Gly Cys Thr Pro Met Val Gly Leu Asp Ser Val Ser Gly Gln Tyr Trp
1               5                   10                  15

Asp Gln His Ala Pro Leu Ala Asp
            20
```

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Gly Pro Cys Pro Met Val Gly Leu Asp Ser Val Ser Gly Gln Tyr Trp
1               5                   10                  15

Asp Gln His Ala Pro Leu Ala Asp
            20
```

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gly Pro Thr Cys Met Val Gly Leu Asp Ser Val Ser Gly Gln Tyr Trp
1               5                   10                  15

Asp Gln His Ala Pro Leu Ala Asp
            20
```

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Gly Pro Thr Pro Cys Val Gly Leu Asp Ser Val Ser Gly Gln Tyr Trp
1               5                   10                  15

Asp Gln His Ala Pro Leu Ala Asp
            20
```

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Gly Pro Thr Pro Met Cys Gly Leu Asp Ser Val Ser Gly Gln Tyr Trp
1               5                   10                  15

Asp Gln His Ala Pro Leu Ala Asp
            20
```

<210> SEQ ID NO 35
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Pro Thr Pro Met Val Cys Leu Asp Ser Val Ser Gly Gln Tyr Trp
1               5                   10                  15

Asp Gln His Ala Pro Leu Ala Asp
            20

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Pro Thr Pro Met Val Gly Cys Asp Ser Val Ser Gly Gln Tyr Trp
1               5                   10                  15

Asp Gln His Ala Pro Leu Ala Asp
            20

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cccacgaatg gataaggcta gcacagattt ctcgtc                              36

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcgtcccgtt cgtgaccgct agccttcaat cccaaac                             37

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtgagaatc caatctagaa cagatttc                                       28

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
aatttctcct ctttaattca gtcctggttg atgc                              34
```

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
taaagaggag aaattaaatg tacgaattaa acgacgg                           37
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
tcgccaaaag cttcttcaat c                                            21
```

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
catgaatgtc tagagctaaa tgaaag                                       26
```

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
cttcacaggt caagcttctt caatc                                        25
```

<210> SEQ ID NO 45
<211> LENGTH: 51
<212> TYPE: PRT
<213> ORGANISM: Asticcacaulis excentricus

<400> SEQUENCE: 45

Met His Thr Pro Ile Ile Ser Glu Thr Val Gln Pro Lys Thr Ala Gly
1               5                   10                  15

Leu Ile Val Leu Gly Lys Ala Ser Ala Glu Thr Arg Gly Leu Ser Gln
            20                  25                  30

Gly Val Glu Pro Asp Ile Gly Gln Thr Tyr Phe Glu Glu Ser Arg Ile
        35                  40                  45

Asn Gln Asp
    50

<210> SEQ ID NO 46
<211> LENGTH: 49
<212> TYPE: PRT
<213> ORGANISM: Asticcacaulis excentricus

```
<400> SEQUENCE: 46

Met Thr Lys Arg Thr Thr Ile Ala Ala Arg Arg Val Gly Leu Ile Asp
1               5                   10                  15

Leu Gly Lys Ala Thr Arg Gln Thr Lys Gly Leu Thr Gln Ile Gln Ala
            20                  25                  30

Leu Asp Ser Val Ser Gly Gln Phe Arg Asp Gln Leu Gly Leu Ser Ala
        35                  40                  45

Asp

<210> SEQ ID NO 47
<211> LENGTH: 49
<212> TYPE: PRT
<213> ORGANISM: Asticcacaulis excentricus

<400> SEQUENCE: 47

Met Arg Thr Tyr Asn Arg Ser Leu Pro Ala Arg Ala Gly Leu Thr Asp
1               5                   10                  15

Leu Gly Lys Val Thr Thr His Thr Lys Gly Pro Thr Pro Met Val Gly
            20                  25                  30

Leu Asp Ser Val Ser Gly Gln Tyr Trp Asp Gln His Ala Pro Leu Ala
        35                  40                  45

Asp

<210> SEQ ID NO 48
<211> LENGTH: 23
<212> TYPE: PRT
<213> ORGANISM: Asticcacaulis excentricus
<220> FEATURE:
<223> OTHER INFORMATION: Contains a residue 1 to 9 covalent bond

<400> SEQUENCE: 48

Gly Leu Ser Gln Gly Val Glu Pro Glu Ile Gly Gln Thr Tyr Phe Glu
1               5                   10                  15

Glu Ser Arg Ile Asn Gln Asp
            20
```